(12) United States Patent
Gratia et al.

(10) Patent No.: US 10,680,180 B2
(45) Date of Patent: Jun. 9, 2020

(54) SMALL MOLECULE HOLE TRANSPORTING MATERIAL FOR OPTOELECTRONIC AND PHOTOELECTROCHEMICAL DEVICES

(71) Applicants: ECOLE POLYTECHNIQUE FEDERALE DE LAUSANNE (EPFL), Lausanne (CH); KAUNAS UNIVERSITY OF TECHNOLOGY, Kaunas (LT)

(72) Inventors: Paul Gratia, Sion (CH); Mohammad Khaja Nazeeruddin, Ecublens (CH); Michael Graetzel, St-Sulpice (CH); Vytautas Getautis, Kaunas (LT); Artiom Magomedov, Kaunas (LT); Tadas Malinauskas, Kaunas (LT); Maryte Daskeviciene, Jovana (LT)

(73) Assignees: Ecole Polytechnique Federale de Lausanne (EPFL), Lausanne (CH); Kaunas University of Technology, Kaunas (LT)

( * ) Notice: Subject to any disclaimer, the term of this patent is extended or adjusted under 35 U.S.C. 154(b) by 161 days.

(21) Appl. No.: 15/554,373

(22) PCT Filed: Mar. 1, 2016

(86) PCT No.: PCT/IB2016/051115
§ 371 (c)(1),
(2) Date: Aug. 29, 2017

(87) PCT Pub. No.: WO2016/139570
PCT Pub. Date: Sep. 9, 2016

(65) Prior Publication Data
US 2018/0033973 A1 Feb. 1, 2018

(30) Foreign Application Priority Data

Mar. 2, 2015 (EP) .................................... 15157217

(51) Int. Cl.
*H01L 31/00* (2006.01)
*H01L 51/00* (2006.01)
(Continued)

(52) U.S. Cl.
CPC ........ *H01L 51/0061* (2013.01); *C07D 209/88* (2013.01); *C09B 57/007* (2013.01);
(Continued)

(58) Field of Classification Search
None
See application file for complete search history.

(56) References Cited

U.S. PATENT DOCUMENTS

| | | |
|---|---|---|
| 2006/0051690 A1 | 3/2006 | Matoliukstyte et al. |
| 2008/0145699 A1 | 6/2008 | Yabe et al. |
| 2009/0021146 A1 | 1/2009 | Iida et al. |

FOREIGN PATENT DOCUMENTS

| | | |
|---|---|---|
| EP | 0758337 B1 | 12/1996 |
| EP | 0613466 B1 | 3/2001 |

(Continued)

OTHER PUBLICATIONS

Xu et al., Carbazole-Based Hole-Transport Materials for Efficient Solid-State Dye-Sensitized Solar Cells and Perovskite Solar Cells, Advanced Materials, 2014, Abstract and pp. 6629-6634, vol. 26, 2014. (Year: 2014).*

(Continued)

*Primary Examiner* — Thanh Truc Trinh
(74) *Attorney, Agent, or Firm* — Taft Stettinius & Hollister LLP

(57) ABSTRACT

The present invention relates to a compound of formula (I) based on carbazole substituted by diphenylamine and used as organic hole conductors or hole transporting material in an optoelectronic or photoelectrochemical device, with (I), D being selected from formula (1) or (2):

(Continued)

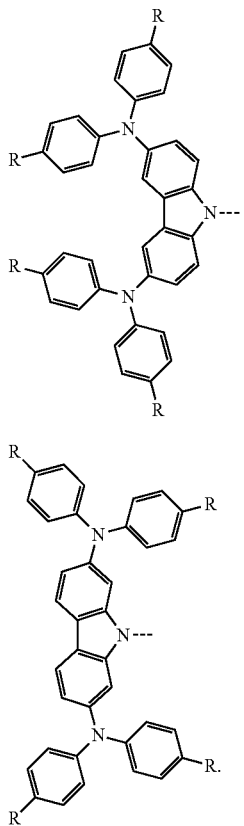

(51) Int. Cl.
  *C07D 209/88* (2006.01)
  *C09B 57/00* (2006.01)
  *H01G 9/20* (2006.01)
  *H01L 51/42* (2006.01)

(52) U.S. Cl.
  CPC ......... *H01G 9/2018* (2013.01); *H01G 9/2059* (2013.01); *H01L 51/0032* (2013.01); *H01L 51/0072* (2013.01); *H01L 51/0077* (2013.01); *H01L 51/4226* (2013.01); *Y02E 10/549* (2013.01)

(56) References Cited

FOREIGN PATENT DOCUMENTS

| | | |
|---|---|---|
| EP | 0983282 B1 | 11/2003 |
| EP | 1622178 A1 | 2/2006 |
| EP | 1990373 A1 | 11/2008 |
| EP | 2703468 A1 | 3/2014 |
| EP | 2883915 A1 | 6/2015 |
| WO | 2006038823 A1 | 4/2006 |
| WO | 2007100033 A1 | 9/2007 |
| WO | 2009098643 A2 | 8/2009 |
| WO | 2009107100 A2 | 9/2009 |
| WO | 2010055471 A1 | 5/2010 |
| WO | 2010094636 A1 | 8/2010 |
| WO | 2010111242 A2 | 9/2010 |
| WO | 2011039715 A1 | 4/2011 |
| WO | 2013057538 A1 | 4/2013 |
| WO | 2014033582 A2 | 3/2014 |
| WO | 2014133121 A1 | 9/2014 |
| WO | 2015087210 A1 | 6/2015 |

OTHER PUBLICATIONS

International Search Report; European Patent Office; International Application No. PCT/IB2016/051115; dated May 18, 2016; 4 pages.
Written Opinion of the International Searching Authority; European Patent Office; International Application No. PCT/IB2016/051115; dated May 18, 2016; 5 pages.
Bo Xu et al.; Carbazole-Based Hole-Transport Materials for Efficient Solid-State Dye-Sensitized Solar Cells and Perovskite Solar Cells; Advanced Materials; 2014; pp. 6629-6634; vol. 26; Copyright 2014 Wiley-VCH Verlag GmbH & Co. KGaA, Weinheim.
Henry J. Snaith et al.; Efficiency Enhancements in Solid-State Hybrid Solar Cells via Reduced Charge Recombination and Increased Light Capture; Nano Letters; 2007; pp. 3372-3376; vol. 7 No. 11; Copyright 2007 American Chemical Society.
Tomas Leijtens et al.; Hole Transport Materials with Low Glass Transition Temperatures and High Solubility for Application in Solid-State Dye-Sensitized Solar Cells; ACS Nano; 2012; pp. 1455-1462; vol. 6 No. 2; Copyright 2012 American Chemical Society.
Lioz Etgar et al.; Mesoscopic CH3NH3PbI3/TiO2 Heterojunction Solar Cells; JACS (Journal of the American Chemical Society); 2012; pp. 17396-17399; vol. 134; Copyright 2012 American Chemical Society.
C.R. Kagan et al.; Organic-Inorganic Hybrid Materials as Semiconducting Channels in Thin-Film Field-Effect Transistors; Science; Oct. 29, 1999; pp. 945-947; vol. 286; www.sciencemag.org.

\* cited by examiner

15 Claims, 4 Drawing Sheets

SMALL MOLECULE HOLE TRANSPORTING MATERIAL FOR OPTOELECTRONIC AND PHOTOELECTROCHEMICAL DEVICES

CROSS REFERENCE To RELATED APPLICATIONS

This application is a U.S. national stage filing of International Application No. PCT/IB2016/051115 filed on Mar. 1, 2016, which claims priority to European Patent Application No. 15157217.9 filed on Mar. 2, 2015, the contents of each application incorporated herein by reference in their entirety.

TECHNICAL FIELD

The present invention relates to hole transporting compound, to organic hole conductors and to hole transporting material comprising such a compound, to optoelectronic photoelectrochemical devices comprising such hole transporting material or hole transporting compound, in particular photovoltaic devices, organic-inorganic perovskite films or layer photovoltaic devices, p-n heterojunctions, dye-sensitized solar cells, organic solar cells and solid state solar cells. The invention is also concerned with a method of preparing such organic hole conductor, layers, and optoelectronic devices.

PRIOR ART AND THE PROBLEM UNDERLYING THE INVENTION

The conversion of solar energy to electrical current using thin film third generation photovoltaics (PV) is being widely explored for the last two decades. The sandwich/monolithic-type PV devices, consisting of a mesoporous photoanode with an organic/inorganic light harvester, redox electrolyte/solid-state hole conductor, and counter electrode, have gained significant interest due to the ease of their fabrication, the flexibility in the selection of materials and the low cost effective production.

Perovskite based materials for optoelectronic applications were known in the literature since the pioneering work by Kagan et al. (C. R. Kagan, D. B. Mitzi, C. D. Dimitrakopoulos; Science, 1999, 286, 945). Recently, the organometallic halide perovskite based on tin ($CsSnX_3$) or lead ($CH_3NH_3PbX_3$) (Etgar, L. et al.; J. Am. Chem. Soc. 2012, 134, 17396-17399) have been introduced as light harvester to replace traditional metal-organic complex or organic molecules in photovoltaic cell. In 2010, Grätzel and Snaith (Snaith, H. J.; Moule, A. J.; Klein, C.; Meerholz, K.; Friend, R. H.; Gratzel, M. Nano Lett.; (Letter); 2007; 7(11)) developed a solid state solar cell using spiro-OMeTAD (2,2',7,7'-tetrakis(N,N-di-p-methoxyphenylamine)-9,9'-spirobifluorene) as organic hold transporting material (HTM) in combination with the hybrid organic-inorganic perovskite $CH_3NH_3PbX_3$, X being ($Cl^-$, $Br^-$ or $I^-$. Currently the best efficiencies in dye sensitized solar cells with solid hole conductors are obtained with the compound spiro-MeO-TAD.

However the use of spiro-OMeTAD as hole transporting material may trigger instability in solar cells and in particular solid state solar cells. Because Spiro-OMeTAD has two oxidation potentials being very close, this hole transporting material in the oxidized form is able to forms a di-cation, which in turn can dismutate and might cause device instability. Further, in many cases, the photocurrent is directly dependent on the yield in the hole transition from the absorber (oxidized perovskite or dye) to the solid p-conductor. This yield depends essentially on two factors: first on the degree of penetration of the p-semiconductor into the oxide pores of the n-conductive metal oxide of the working electrode, and second on the thermodynamic driving force for the charge transfer, i.e. especially on the difference in the free enthalpy $\Delta G$ between dye and p-conductor. Since spiro-OMeTAD compound is present in semi-crystalline form, there is the risk that it will (re)crystallize in the processed form in the solar cell. In addition, the solubility in customary process solvents is relatively low, which leads to a correspondingly low degree of pore filling. Along stability issues, the high cost due to a complicated synthetic route and the high purity that is required (sublimation grade) in order to have good performance have been the main drawbacks for commercial applications of solid state solar cells.

A number of studies have focused on replacing spiro-OMeTAD with alternative high-mobility hole conductors. Organic polymers such as polypyrrole, poly(3,4-ethylenedioxythiophene), carbazole-based polymers, polyaniline, poly(4-undecyl-2,2'-bithiophene), poly(3-octylthiophene), poly(triphenyldiamine) and poly(N-vinylcarbazole) are used as solid p-semiconductors, although the polymers are typically not used in pure form but usually in a mixture with additives. Compounds based on triarylamine being used as hole conductors in organic solar cells are disclosed in WO 2010/094636. However, none of these compounds and polymers has shown similar performance than spir-OMeTAD up to now, US 2008/0145699 and US 2009/0021146 concerns compounds based on carbazolyl groups being used as hole and electron transporting material in electron inorganic electroluminescent device, and providing a device emitting light with a high efficiency an being highly stable driven.

The present invention addresses the disadvantage of organic hole transporting material, which provides instability to the device, when said hole transporter material is in oxidized form, as it is the case of spiro-OMeTAD.

The present invention also pursues to provide new hole transporting material, which does not required a step of sublimation during its purification after its synthesis as it is the case of the synthesis of spiro-OMeTAD and presents case to be synthesized.

The present invention also pursues to provide new hole transporting material, which provides higher power conversion efficiency (PCE) to photovoltaic devices comprising perovskite or organic or organometallic dyes as sensitizer or light absorbing material as well as to further optoelectronic devices Organic Light Emitting Diodes (OLED), Field effect Transistors (FET).

The present invention addresses the disadvantage due to the high prices of hole transporting materials and their expensive and complex synthesis. The synthesis process of hole transporting material involves expensive starting material compounds being not commercially available, very low temperature of reaction step, complexity, aggressive reagents and numerous steps (e.g. 5 steps for the Spiro-OMetTAD synthesis). Thus the synthesis process is lengthy, time-consuming and expensive and causes non-negligible environmental impact.

The invention pursues to provide an efficient solar cell, which can be rapidly prepared in an efficient way, using readily available or low cost materials such as conductive material, using a short manufacturing procedure based on industrially known manufacturing step, keeping the material costs and the material impact on the environment very low.

The present invention addresses the problems depicted above.

SUMMARY OF THE INVENTION

Remarkably, in some aspects, the present inventors have found that a compound based on diphenylamine substituted carbazole operates as a hole transporting material and improves the PCE of optoelectronic and/or photoelectrochemical device, and in particular optoelectronic and/or photoelectrochemical device comprising perovskite pigment as sensitizer.

The specific configuration of the structure of the compounds based on diphenylamine substituted carbazole (donor moiety) acts as hole conductor compound or material. Although their large size, said compounds are good soluble in organic solvent, which greatly facilitates their purification and processing and their application or deposition on the sensitizer layer in the solid photovoltaic device. Moreover the synthesis process of these compounds involves two steps and starting materials easily available.

In an aspect, the present invention provides compound of formula (I):

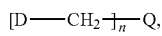
(I)

wherein
n is 2, 3, 4, 6 or 8;
Q is a mono- or polycyclic system comprising at least one pair of a conjugated double bond (—C=C—C=C—), the polycyclic system comprising fused aromatic rings or monocyclic aromatic rings bound together by covalent bond, said mono- or polycyclic system being substituted by H, halogen, cyano group, C1-C20 cyanoalkyl group, C1-C20 alkyl, C1-C20 alkoxy group, C1-C20 alkoxyalkyl, C1-C20 haloalkyl group, C1-C20 haloalkoxyalkyl, wherein said cyanoalkyl, alkyl, alkoxy, alkoxyalkyl, haloalkyl, haloalkoxyalkyl, if they comprise 3 or more carbons, may be linear, branched or cyclic, wherein halogen is selected from Cl, F, Br, or I, and wherein Q is linked to D through a methylene bridge, divalent alkyl or methanediyl bond —CH$_2$—;

D is a heteroaromatic polycyclic system being independently selected front formula (1) or (2):

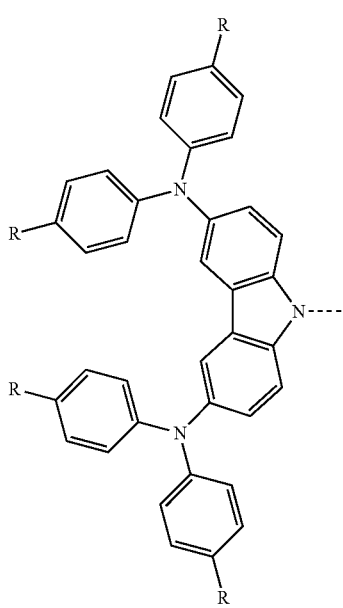
(1)

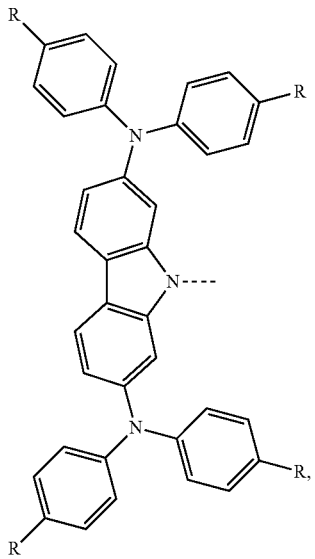
(2)

wherein
the dotted lines represent the bond by which D is connected to methylene bridge or methanediyl bond —CH$_2$—;
R is a substituent, on each occurrence, identically or differently selected from halogen, C1-C9 alkoxy group, C1-C9 alkoxyalkyl, C1-C9 alkyl group, C1-C9 haloalkoxy group, C1-C9 haloalkoxyalkyl, C1-C9 haloalkyl, C4-C20 aryl, C4-C20 heteroaryl, C4-C20 alkylaryl group, C4-C20 aryloxy group or C4-C20 heteroaryloxy group, heteroatoms being selected from O, S, Se, Si and halogen being selected F or Cl; wherein said alkyl, alkoxy, alkoxylalkyl, haloalkyl, haloalkoxy and haloalkoxyalkyl, if they comprise 3 or more carbons, may be linear, branched or cyclic and wherein said heteraryl, aryloxy group, heteroaryloxy group are unsubstituted or substituted by C1-C20 alkyl or C1-C20 heteroalkyl, wherein said alkyl and heteroalkyl, if they comprise 3 or more carbons, may be linear, branched or cyclic.

In a further aspect, the invention provides a hole transporting material comprising at least one small molecule hole transporting material being selected from one of compounds of the invention.

In another aspect, the invention provides an optoelectronic and/or photoelectrochemical device comprising a compound of the invention.

In a particular embodiment, the invention specifically provides an optoelectronic or photoelectrochemical device, which is a photovoltaic, solid state device or a solid state solar cell further comprising an organic-inorganic perovskite as sensitizer under the form of a layer.

In a further aspect, the invention provides use of a compound of the invention as a hole transporting material in optoelectronic or photoelectrochemical device.

Further aspects and preferred embodiments of the invention are detailed herein below and in the appended claims. Further features and advantages of the invention will become apparent to the skilled person from the description of the preferred embodiments given below.

DETAILED DESCRIPTION OF THE PREFERRED EMBODIMENTS

Figure 1:
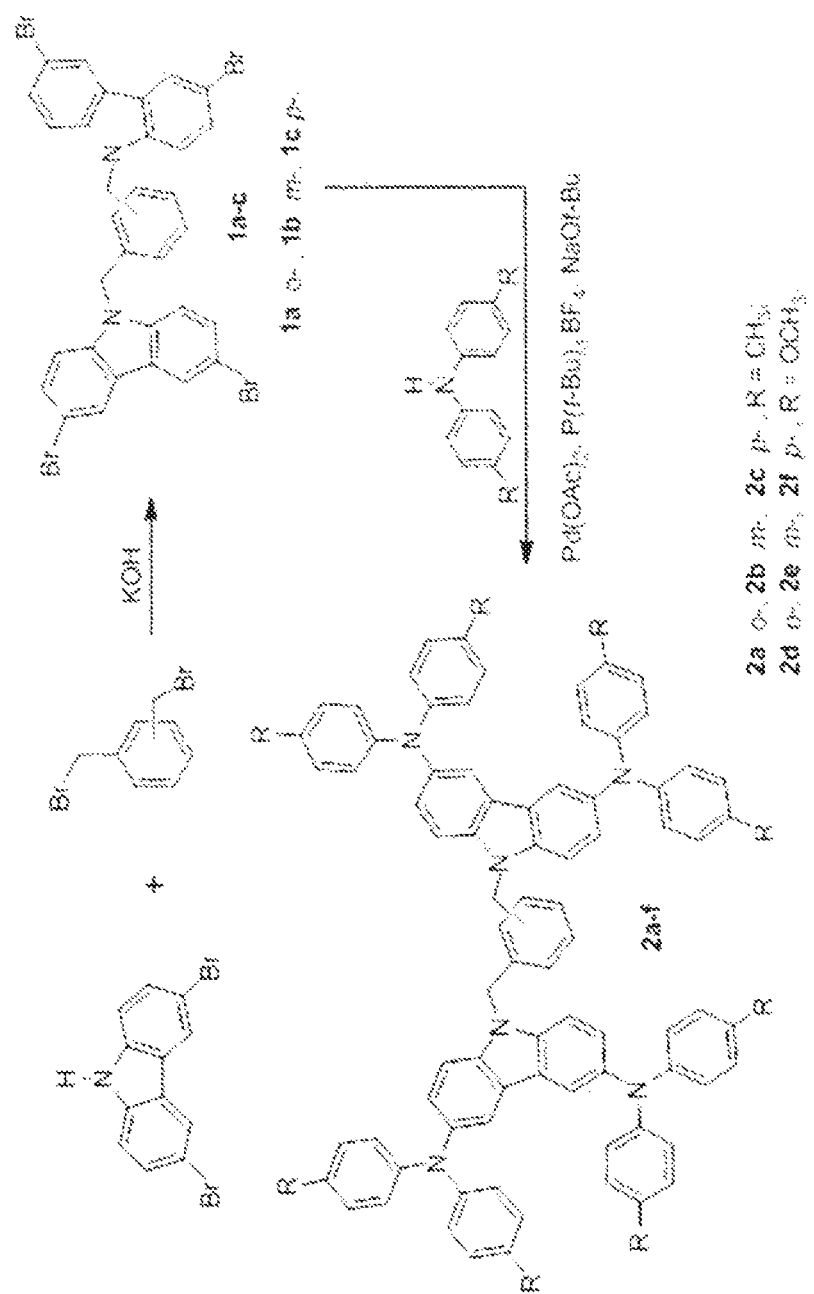
FIG. 1 shows the schematic synthesis route of compounds of the invention based on diphenylamine substituted carbazole. Intermediate compounds 1a, 1b and 1c and final compound 2a (corresponding to compound (22) or V-931), final compound 2b (corresponding to compound (24) or V-928), final compound 2c (corresponding to compound (26) or V-908), final compound 2d (corresponding to compound (21) or V-886), final compound 2e (corresponding to compound (23) or V-885), and final compound 2f (corresponding to compound (25) or V-911) are described.
Figure 2:
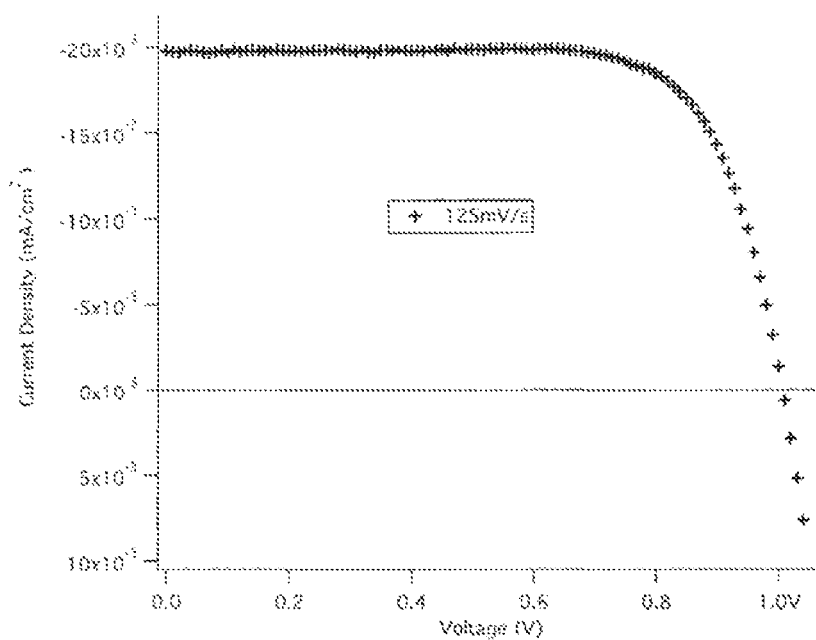
FIG. 2 shows the Current-Voltage curve of compound (22) corresponding to compound V-886.

The present invention concerns a compound based on diphenylamine substituted carbazole of formula (I).

In particular, the present invention concerns a compound of formula (I)

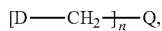
(I)

wherein n is 2, 3, 4, 6 or 8;

Q is a mono- or polycyclic system comprising at least one pair of a conjugated double bond (—C=C—C=C—), the polycyclic system comprising fused aromatic rings or monocyclic aromatic rings bound together by covalent bond, said mono- or polycyclic system being substituted by H, halogen, cyano group, C1-C20 cyanoalkyl group, C1-C20 alkyl, C1-C20 alkoxy group, C1-C20 alkoxyalkyl, C1-C20 haloalkyl group, C1-C20 haloalkoxyalkyl, wherein said cyanoalkyl, alkyl, alkoxy, alkoxyalkyl, haloalkyl, haloalkoxyalkyl, if they comprise 3 or more carbons, may be linear, branched or cyclic, wherein halogen is selected from Cl, F, Br, or I, and wherein Q is linked to D through a methylene bridge, divalent alkyl or methanediyl bond —CH$_2$—;

D is a heteroaromatic polycyclic system being independently selected from formula (1) or (2):

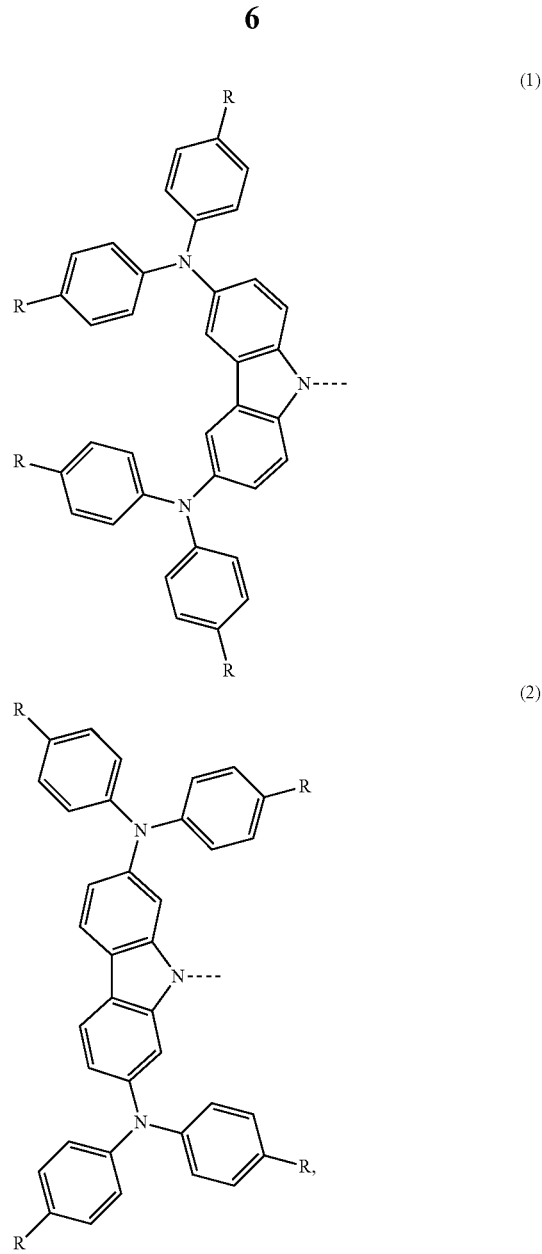

wherein
the dotted lines represent the bond by which D is connected to methylene bridge or methanediyl bond —CH$_2$—;
R is a substituent, on each occurrence, identically or differently selected from halogen, C1-C9 alkoxy group, C1-C9 alkoxyalkyl, C1-C9 alkyl group, C1-C9 haloalkoxy group C1-C9 haloalkoxyalkyl, C1-C9 haloalkyl, C4-C20 aryl, C4-C20 heteraryl, C4-C20 alkylaryl group, C4-C20 aryloxy group or C4-C20 heteraryloxy group, heteratoms being selected from O, S, Se, Si and halogen being selected from F or Cl, and wherein said alkyl, alkoxy, alkoxylalkyl, haloalkyl, haloalkoxy and haloalkoxyalkyl, if they comprise 3 or more carbons, may be linear, branched or cyclic and wherein said heteraryl, aryloxy group, heteraryloxy group are unsubstituted or substituted by C1-C20 alkyl or C1-C20 heteroalkyl, wherein said alkyl and heteroalkyl, if they comprise 3 or more carbons, may be linear, branched or cyclic.

In particular R is a substituent, on each occurrence, identically or differently selected from halogen, C1-C9 alkyl, C1-C9 alkoxy group, C1-C9 alkoxyalkyl, C1-C9 haloalkoxy group or C1-C9 haloalkoxyalkyl group, said alkyl, alkoxy, alkoxyalkyl, haloalkyl, haloalkoxy and haloalkoxyalkyl, if they comprise 3 or more carbons, are linear, branched or cyclic, preferably linear or branched. In a preferred embodiment, R is selected from halogen, C1-C7 alkyl, Cl alkoxy group, C1-C7 alkoxyalkyl, C1-C9 haloalkoxy group or C1-C9 haloalkoxyalkyl group.

In another embodiment, substituents R of the same heteroaromatic polycyclic system D according to any one of the formulae (1) or (2) are identical. R substituents of D of formula (1) may be identical to each other and/or identical to those of D of formula (2).

In a further embodiment, R is a substituent, on each occurrence, identically selected from halogen, C1-C9 alkyl, C1-C9 alkoxy group, C1-C9 alkoxyalkyl, C1-C9 haloalkoxy group or C1-C9 haloalkoxyalkyl group, said alkyl, alkoxy, alkoxylalkyl, haloalkyl, haloalkoxy and haloalkoxyalkyl, if they comprise 3 or more carbons, are linear, branched or cyclic.

Preferably alkoxy, alkoxyalkyl, alkyl group, haloalkoxy group, haloalkoxyalkyl, haloalkyl, aryl, heteraryl, alkylaryl, aryloxy or heteraryloxy of substituent R of D moieties according to any one of formulae (1) or (2) are selected from hydrocarbon, hydrocarbyl, heterocarbon or heterocarbyl and from aromatic hydrocarbon, aromatic hydrocarbyl, aromatic heterocarbon or aromatic heterocarbyl containing from 1 to 9 carbons, 1 to 7 carbons, 4 to 20 carbons, 4 to 16 carbons or 4 to 7 carbons, 0 to 10 heteroatoms being selected from O, S, Se, Si and halogen being selected from F or Cl, and wherein said alkoxy, alkoxyalkyl, alkyl group, haloalkoxy group, haloalkoxyalkyl, haloalkyl, aryl, heteroaryl, alkylaryl, aryloxy or heteroaryloxy, if they comprise 3 or more carbons, may be linear, branched or cyclic.

In another embodiment, the compound of formula (I) comprises a structure selected from any one of formulae (II) to (VI)

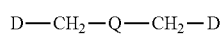

(II)

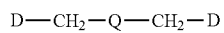

(III)

(IV)

(V)

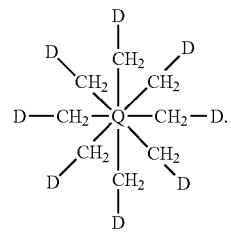

(VI)

Preferably, the compound of formula (I) comprises a structure of formula (II), (III) or (IV). D is defined as above such as for the compound of formula (I).

In an embodiment of the compound of the invention of formula (I) and/or according to any one of formulae (II) to (VI), D is a heteroaromatic polycyclic system of formula (1).

In a further embodiment of the compound of the invention of formula (1) and/or according to any one of formulae (II) to (VI), D is a heteroaromatic polycyclic system of formula (2).

In particular, D of the compound of the compound of the invention of formula (I) and/or according to any one of formulae (II) to (VI) may be the same on each occurrence or being different. A compound of the invention may comprise heteroaromatic polycyclic systems D being all of formula (1) or being all of formula (2) or being of formula (1) and of formula (2).

The moiety Q provides with the methylene bridge the linkage group between at least two moieties D or more depending of the number n of moiety D presents in the compounds of the invention.

In particular, Q is a mono- or polycyclic system comprising at least one pair of a conjugated double bond (—C═C—C═C—), the polycyclic system comprising fused aromatic rings, said mono- or polycyclic system being substituted by H, halogen, cyano group, C1-C20 cyanoalkyl group, C1-C20 alkyl, C1-C20 alkoxy group, C1-C20 alkoxyalkyl, C1-C20 haloalkyl group, C1-C20 haloalkoxyalkyl, wherein said cyanoalkyl, alkyl, alkoxy, alkoxyalkyl, haloalkyl, haloalkoxyalkyl, if they comprise 3 or more carbons, may be linear, branched or cyclic, wherein halogen is selected from Cl, F, Br, or I. Preferably Q is a monocyclic system.

In an embodiment of the compounds of the invention of formula (I) and/or according to any one of formulae (II) to (VI), Q is selected from a moiety according to any one of the formulae (3) to 20)

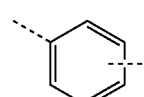

(3)

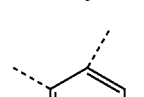

(4)

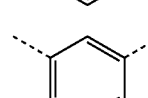

(5)

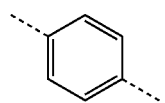
(6)
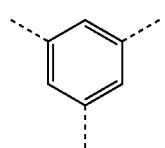
(7)
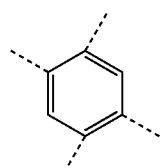
(8)
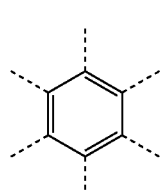
(9)
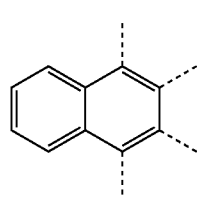
(10)
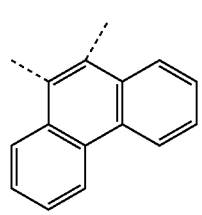
(11)
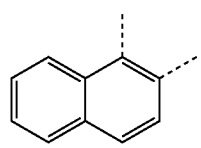
(12)
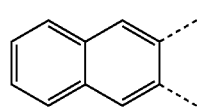
(13)
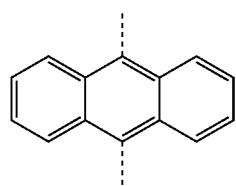
(14)
(15)
(16)
(17)
(18)
(19)
(20)

wherein
the dotted lines represent the bond by which Q is connected to methylene bridge or methanediyl bond —CH$_2$—; $R^1$ to $R^{11}$ substituents independently selected from H, halogen, cyano group, C1-C20 cyanoalkyl group, C1-C20 alkyl, C1-C20 alkoxy group, C1-C20 alkoxyalkyl, C1-C20 haloalkyl group, C1-C20 haloalkoxyalkyl, wherein said cyanoalkyl, alkyl, alkoxy, alkoxyalkyl, haloalkyl, haloalkoxyalkyl, if they comprise 3 or more carbons, may be linear, branched or cyclic, wherein halogen is selected from Cl, F, Br, or I. Preferably $R^1$ to $R^{11}$ are substituents independently selected from H, C1-C20 alkyl, C1-C20 alkoxy group, C1-C20 alkoxyalkyl, wherein said alkyl and alkoxyalkyl, if they comprise 3 or more carbons, may be linear, branched or cyclic.

Preferably cyanoalkyl, alkyl, alkoxy, alkoxyalkyl, haloalkyl, haloalkoxyalkyl being substituents of Q and/or $R^1$ to $R^{11}$ being substituents of Q moiety according to any one of formulae (3) to (20) are selected from hydrocarbon, hydrocarbyl heterocarbon or heterocarbyl containing from 1 to 16 carbons, 1 to 12 carbons, 1 to 9 carbons, 1 to 6 carbons and may contain 0-10 heteroatom being O and 0-1 halogen being selected from Cl, F, Br or I, and being characterized in that, if they comprise 3 or more carbons, they may be linear, branched or cyclic, preferably linear or branched, and if substituting the same moiety Q, they may be identical or different, preferably identical.

In particular, $R^1$ to $R^3$ are selected from C1-C20-alkoxy group, preferably C1-C9 alkoxy group, most preferably Cl alkoxy group; $R^4$ and $R^5$ are selected from C1-C20-alkoxyalkyl group or C1-C20 haloalkyl group, preferably C1-C9 alkoxyalkyl or C1-C9 haloalkyl group, most preferably C8-C9 alkoxyalkyl group or halogen, halogen being Cl, F, Br or I, preferably Cl; $R^6$ to $R^8$ and $R^{11}$ are selected from C1-C20-alkyl group, preferably C1-C9 alkyl, most preferably Cl alkyl group; $R^{10}$ is H and $R^9$ is selected from cyano group, C1-C20 cyanoalkyl group, C1-C9 cyanoalkyl group, preferably cyano group.

In an embodiment of the compound of formula (I) and/or according to any one of formulae (II) to (VI), if n is 2, Q is selected from a moiety according to any one of formulae (3) to (6), (11) to (14), (16), (17) and (20); if n is 3, Q is selected from a moiety according to any one of formulae (7), (15) and (18); if n is 4, Q is selected from a moiety according to any one of formulae (8) and (10); if n is 6, Q is selected from a moiety according to f formula (9); and if n is 8, Q is selected from a moiety according to f formula (19). Preferably n is 2 or 3 and Q is selected from a moiety according to any one of formulae (3) to (6), (11) to (14), (16), (17) and (20) or a moiety according to any one of formulae (7), (15) and (18), respectively.

According to a further embodiment, the compound of the invention of formula (1) is selected from a compound according to any one of formulae (21) to (40)

(21)

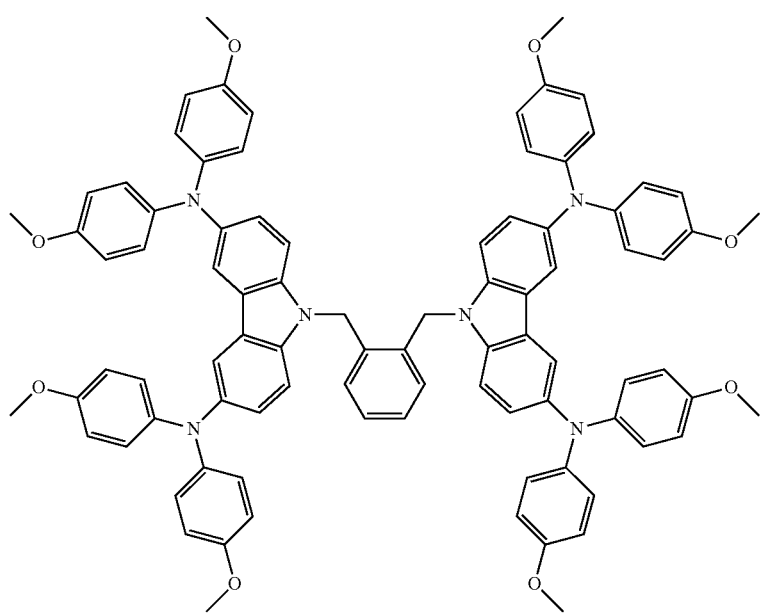

-continued
(22)
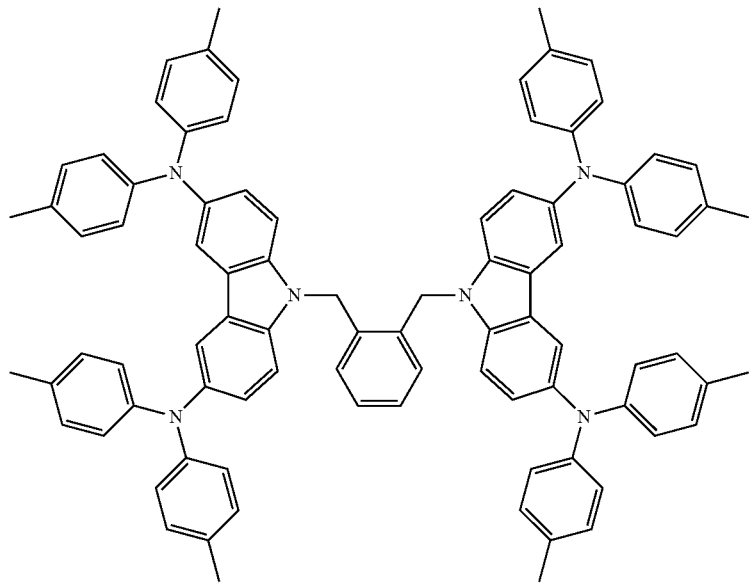
(23)
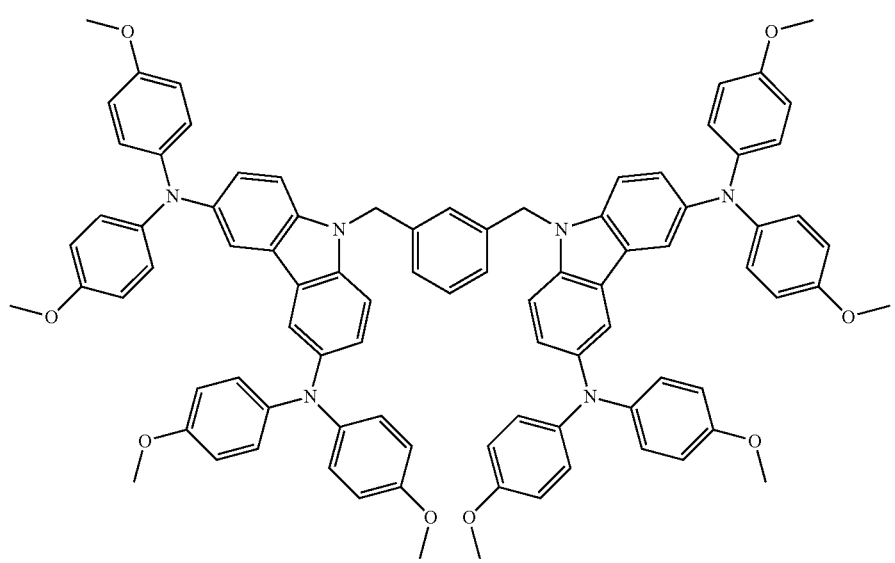
(24)
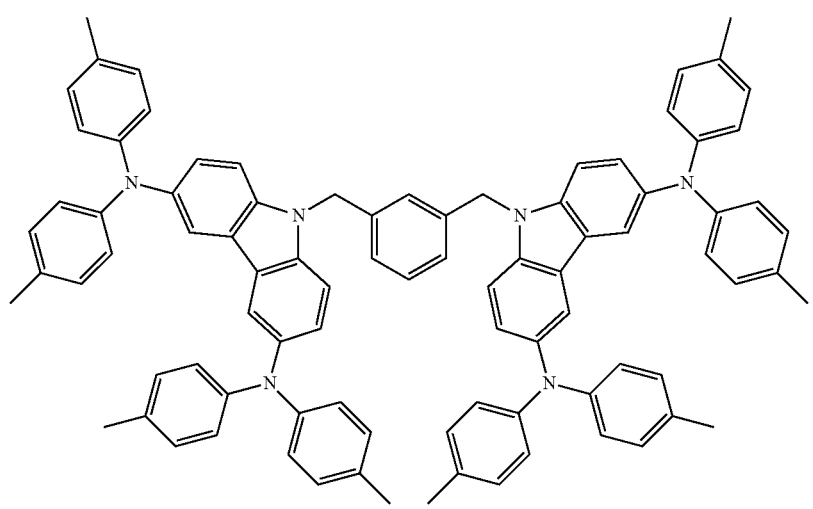

(25)
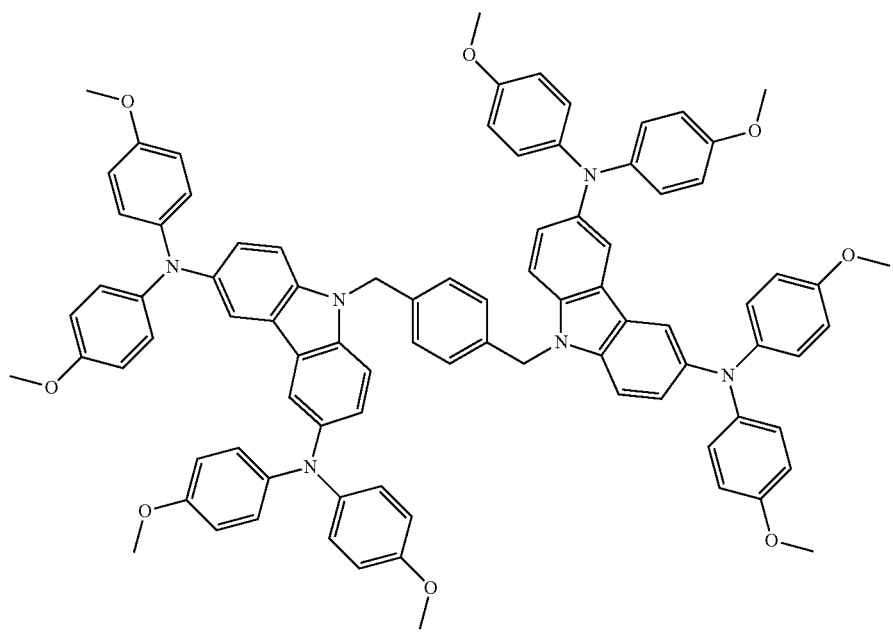
(26)
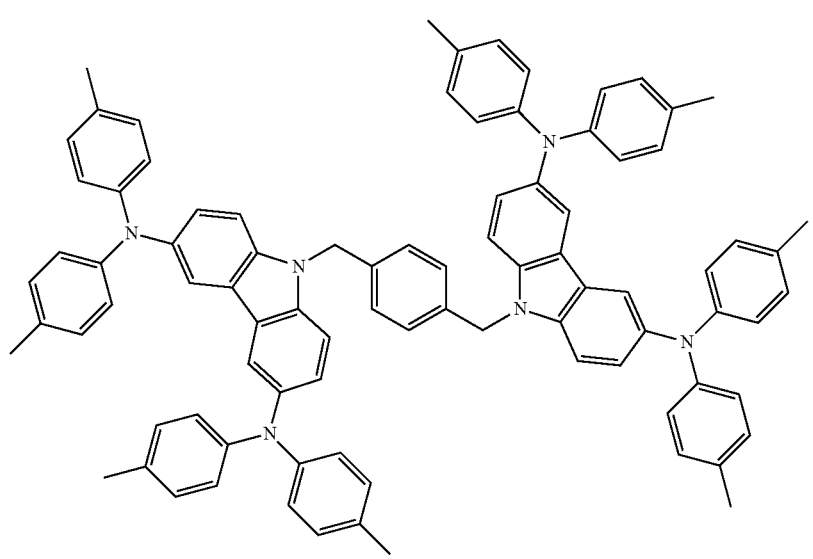

-continued
(27)
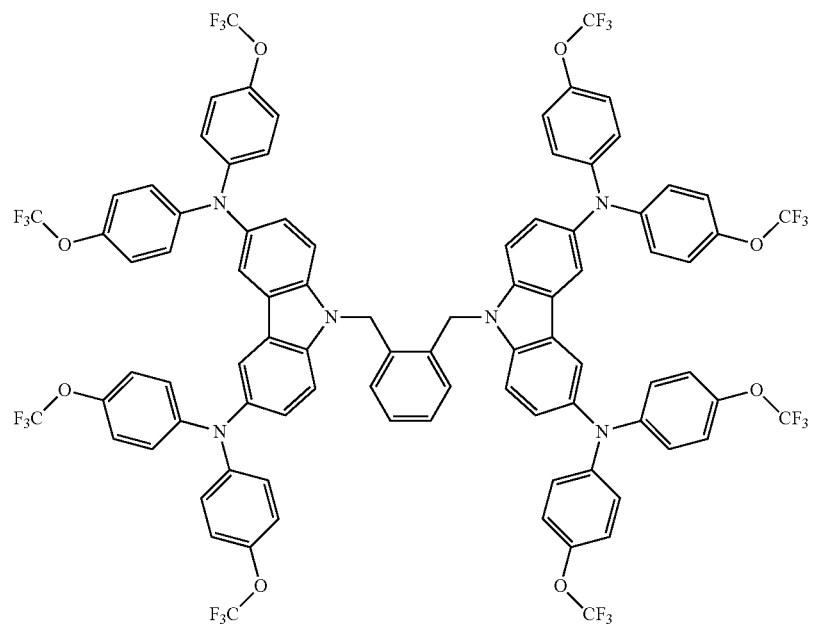
(28)
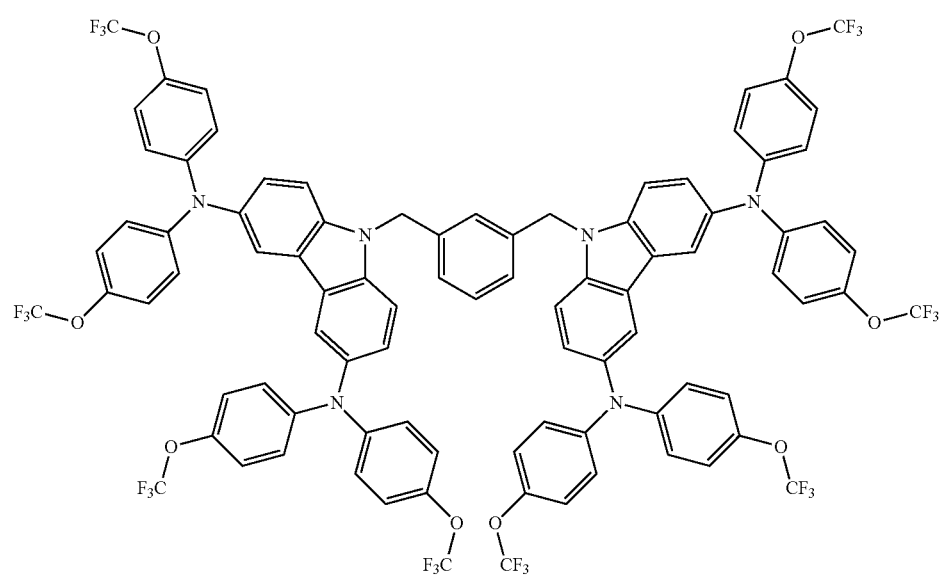

-continued
(29)
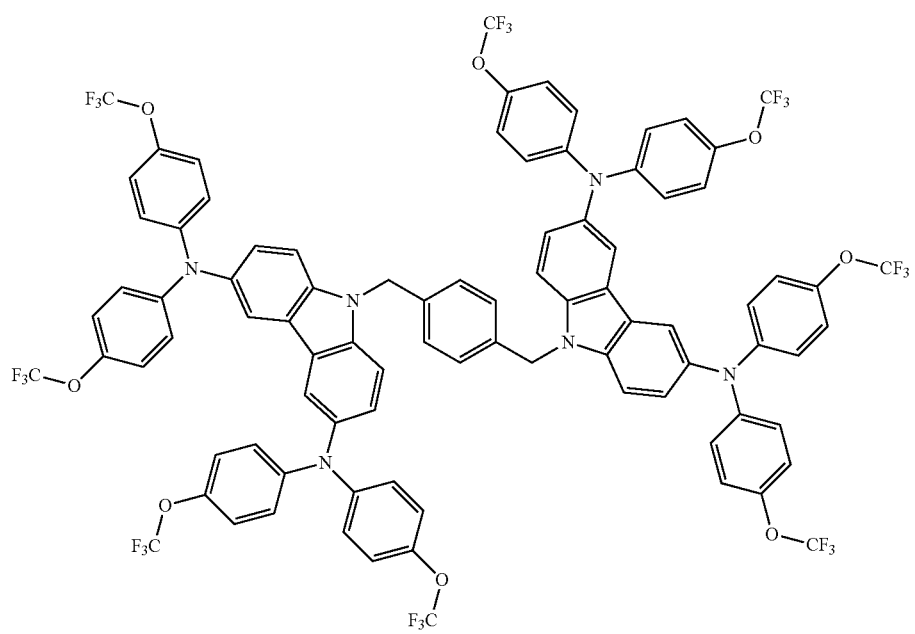
(30)
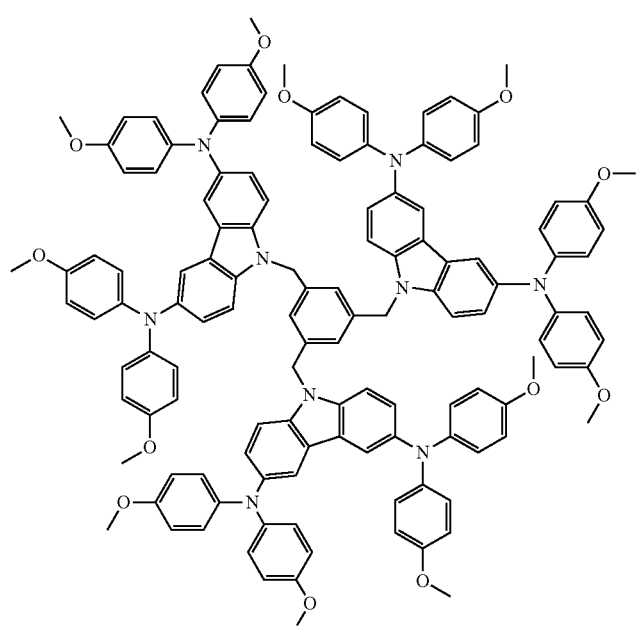

-continued
(31)
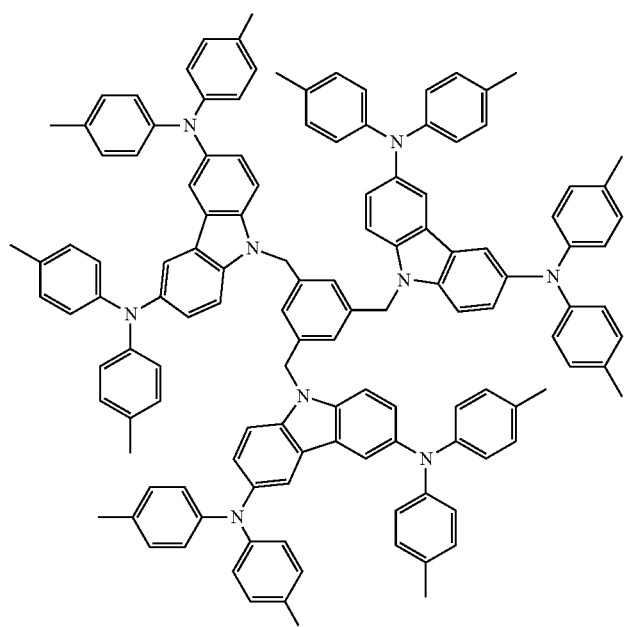
(32)
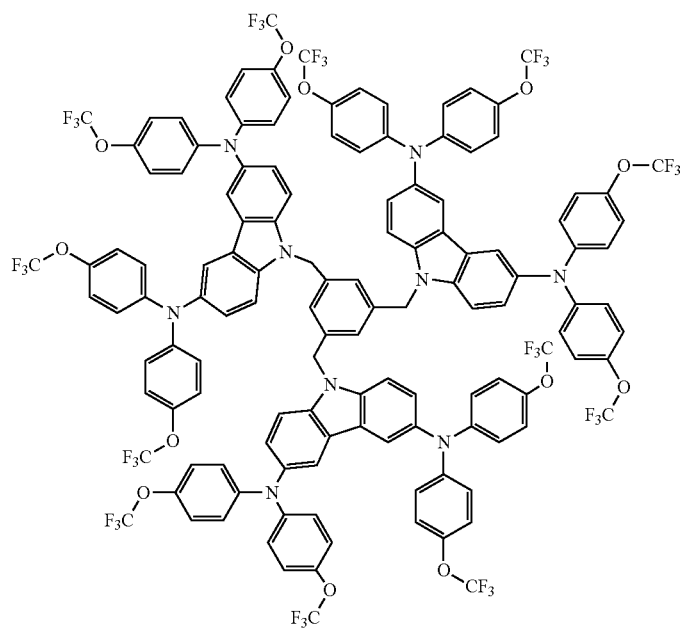

-continued
(33)
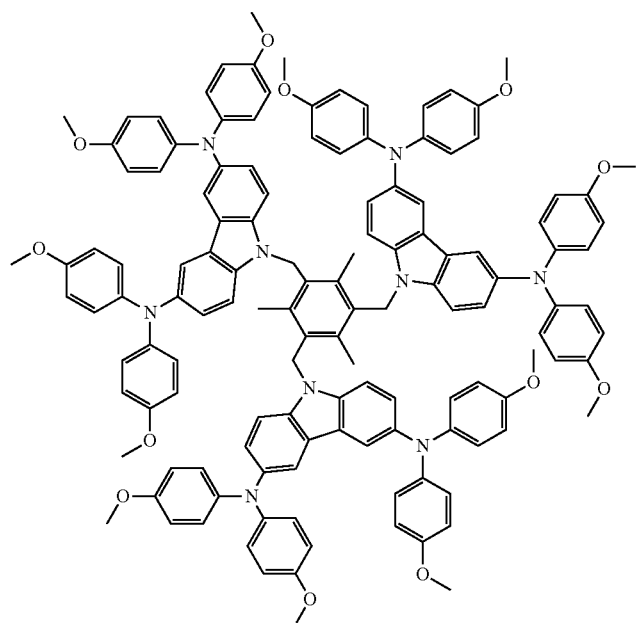
(34)
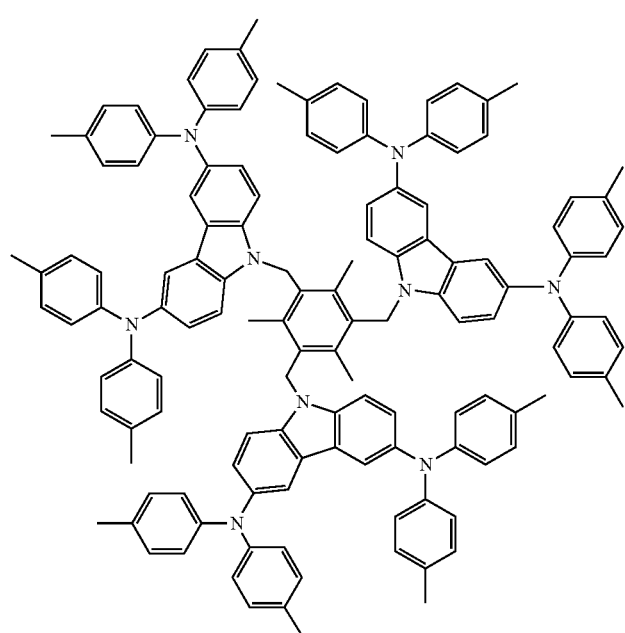

(35)
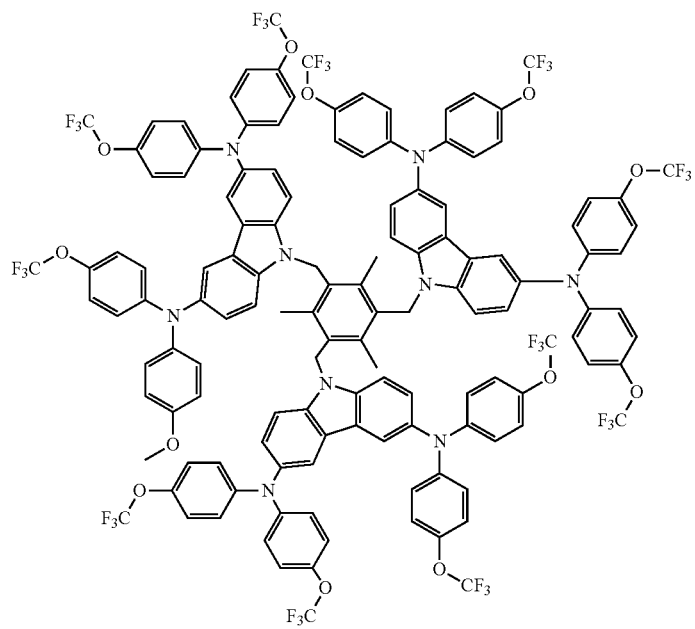
(36)
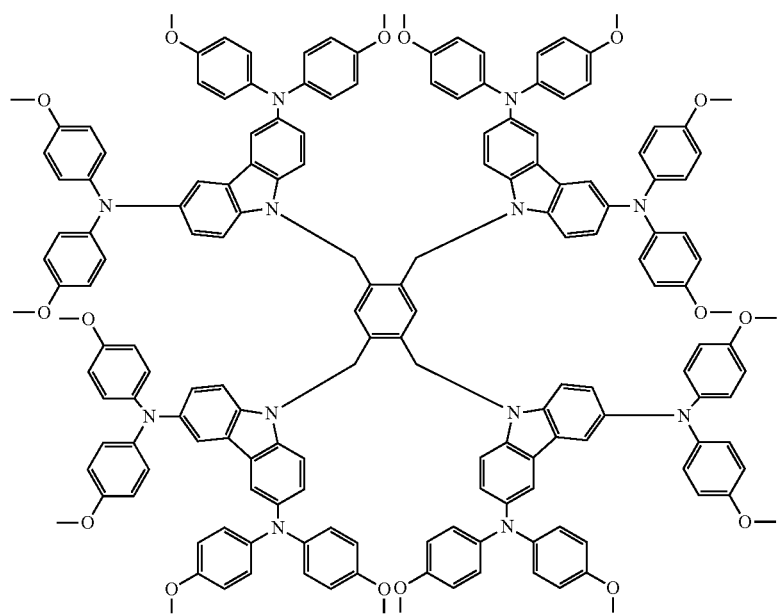

(37)
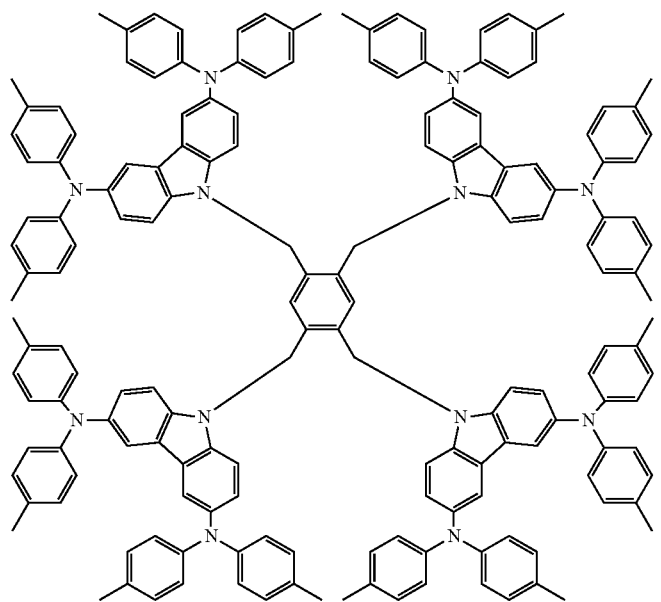
(38)
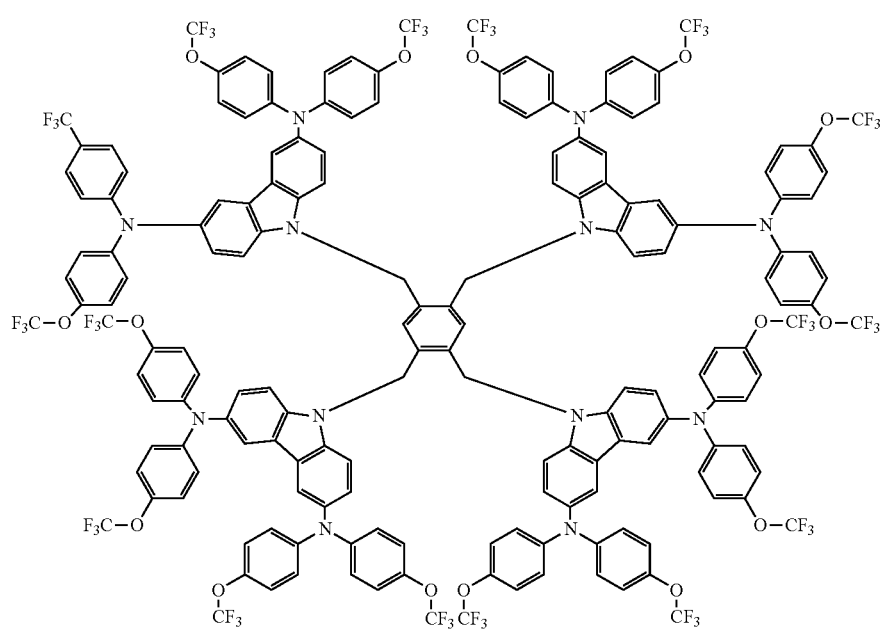

-continued (39)

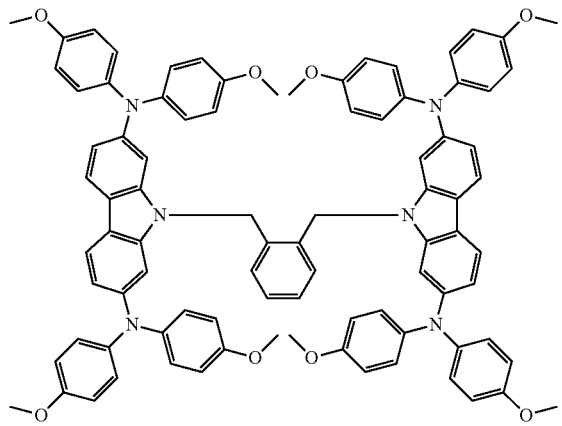

(40)

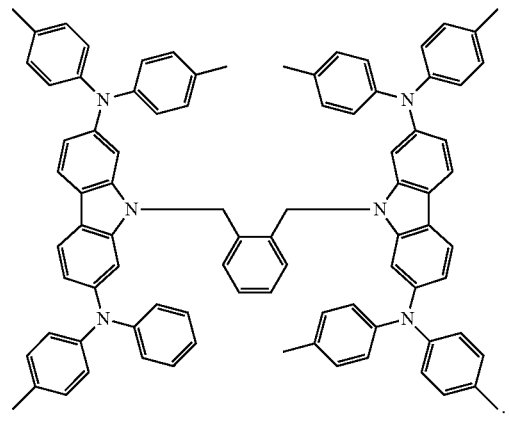

In a further aspect, the invention provides a hole transporting material comprising at least one small molecule hole transporting material being selected from a compound of formula (I) and/or a compound according to any one of formulae (II) to (VI). In particular the hole transporting material comprises at least one compound of formula (I) and/or a compound according to any one of formulae (II) to (VI) or a combination thereof.

The invention also provides in a further aspect an optoelectronic and/or photoelectrochemical device comprising a compound of the invention of formula (I) and/or a compound according to any one of formulae (II) to (VI).

The optoelectronic and/or photoelectrochemical device of the invention comprises a hole transporting material, wherein said hole transporting material comprises a compound of formula (I) and/or a compound according to any one of formulae (II) to (VI).

The optoelectronic and/or photoelectrochemical device of the invention is selected from an organic photovoltaic device, a photovoltaic solid state device, a p-n heterojunction, an organic solar cell, a dye sensitized solar cell, a solid state solar cell, a phototransistor and OLED (organic light-emitting diode).

According to an embodiment, the optoelectronic and/or photoelectrochemical device of the invention is a solar cell selected from an organic solar cell a dye sensitized solar cell or a solid state device.

According to an embodiment, the optoelectronic and/or photoelectrochemical device of the invention, in particular a photovoltaic solid slate device comprises a conducting support layer, a surface-increasing scaffold structure, a sensitizer or sensitizer layer, a hole transporting layer and a counter electrode and/or metal layer.

In a further embodiment, the optoelectronic and/or photoelectrochemical device of the invention is a photovoltaic solid state device being a solid state solar cell comprising an organic-inorganic perovskite as sensitizer under the form of a layer.

In an embodiment, the hole transporting layer of the optoelectronic and/or photoelectrochemical device, in particular a photovoltaic solid state device, is made of a hole transporting material of the invention comprising at least one small molecule hole transporting material being selected from a compound of formula (I) and/or a compound according to any one of formulae (II) to (VI) or a combination thereof. In particular the hole transporting material comprises at least one compound of formula (I) and/or a compound according to any one of formulae (II) to (VI) or a combination thereof.

According to another embodiment, the optoelectronic and/or photoelectrochemical device, in particular a photovoltaic solid state device, comprises a hole collector layer comprising a hole transporting material of the invention, a conductive layer, an electron blocking layer, a sensitizer layer and a current collector layer, wherein the hole collector layer is coated by the conductive layer; wherein the electron blocking layer is between the conductive layer and the sensitizer layer, which is in contact with the current collector layer being a metal or a conductor.

According to a further embodiment, the conductive material is selected from one or more conductive polymers or one or more hole transporting materials, which may be selected from poly(3,4-ethylenedioxythiophene):poly(styrenesulfonate) (PEDOT:PSS), poly(3,4-ethylenedioxythiophene):poly(styrenesulfonate):graphene nanocomposite (PEDOT:PSS:graphene), poly(N-vinylcarbazole) (PVK) and sulfonated poly(diphenylamine) (SPDPA), preferably from PEDOT:PSS, PEDOT:PSS:graphene and PVK, more preferably from PEDOT:PSS. Conductive polymers may also be selected from polymers comprising polyaniline, polypyrrole, polythiophene, polybenzene, polyethylenedioxythiophene, polypropylenedioxy-thiophene, polyacetylene, and combinations of two or more of the aforementioned, for example. The conductive polymer of the photovoltaic solid state device of the invention is preferably selected from the above polymer in a watery dispersion.

For the purpose of the present specification, the expression "in electric contact with" means that electrons or holes can get from one layer to the other layer with which it is in electric contact, at least in one direction. In particular, considering the electron flow in the operating device exposed to electromagnetic radiation, layers through which electrons and/or holes are flowing are considered to be in electric contact. The expression "in electric contact with" does not necessarily mean, and preferably does not mean, that electrons and/or holes can freely move in any direction between the layers.

The conducting support layer is preferably substantially transparent. "Transparent" means transparent to at least a part, preferably a major part of the visible light. Preferably, the conducting support layer is substantially transparent to all wavelengths or types of visible light. Furthermore, the conducting support layer may be transparent to non-visible light, such as UV and IR radiation, for example.

According to an embodiment, the conducting support layer provides the support layer of photovoltaic solid state device. Preferably, the photovoltaic solid state device is built on said support layer. According to another embodiment, the support of photovoltaic solid state device is provided on the side of the counter electrode. In this case, the conductive support layer does not necessarily provide the support of the device, but may simply be or comprise a current collector, for example a metal foil.

The conducting support layer preferably functions and/or comprises a current collector, collecting the current obtained from the photovoltaic solid state device. The conducting support layer may comprise a material selected from indium doped tin oxide (ITO), fluorine doped tinoxide (FTO), $ZnO-Ga_2O_3$, $ZnO-Al_2O_3$, tin-oxide, antimony doped tin oxide (ATO), $SrGeO_3$ and zinc oxide, preferably coated on a transparent substrate, such as plastic or glass. In this case, the plastic or glass provides the support structure of the layer and the cited conducting material provides the conductivity. Such support layers are generally known as conductive glass and conductive plastic, respectively, which are thus preferred conducting support layers in accordance with the invention. According to an embodiment, the conducting support layer comprises a conducting transparent layer, which may be selected from conducting glass and from conducting plastic.

According to an embodiment of the invention, a surface-increasing scaffold structure is provided on said conducting support structure or on a protective layer that may be provided on said scaffold structure.

According to an embodiment of the solar cell and the heterojunction of the invention, the surface-increasing scaffold structure is nanostructured and/or nanoporous. The scaffold structure is thus preferably structured on a nanoscale. The structures of said scaffold structure increase the effective surface compared to the surface of the conductive support.

According to an embodiment, said scaffold structure is made from and/or comprises a metal oxide. For example, the material of the scaffold structure is selected from semiconducting materials, such as Si, $TiO_2$, $SnO_2$, $Fe_2O_3$, ZnO, $WO_3$, $Nb_2O_5$, CdS, ZnS, PbS, $Bi_2S_3$, CdSe, CdTe, $SrTiO_3$, GaP, InP, GaAs, $CuInS_2$, $CuInSe_2$, and combinations thereof, for example. Preferred semiconductor materials are Si, $TiO_2$, $SnO_2$, ZnO, $WO_3$, $Nb_2O_5$ and $SrTiO_3$, for example. According to an embodiment, the surface-increasing scaffold structure is nanostructured and/or nanoporous.

The invention does not intend to exclude the possibility that there are one or more intermediate layers between the scaffold structure and the conductive support. Such intermediate layers, if present, would preferably be conducting and/or semiconducting.

According to an embodiment, the sensitizer layer of the photovoltaic solid state device comprising at least one pigment being selecting from organic, inorganic, organometallic and organic-inorganic pigments or a combination thereof. The sensitizer is preferably a light absorbing compound or material. Preferably, the sensitizer is a pigment, and most preferably the sensitizer is an organic-inorganic pigment.

The sensitizer layer may comprise one or more pigments of the group consisting of organometallic sensitizing compounds (phthalocyanine derived compounds, porphyrine derived compounds), metal free organic sensitizing compounds (diketopyrrolopyrrole (DPP) based sensitizer), inorganic sensitizing compounds such as quantum dots, $Sb_2S_3$ (Antimonysulfide, for example in the form of thin films), aggregates of organic pigments, nanocomposites, in particular organic-inorganic perovskites, and combinations of the aforementioned. For the purpose of the invention, it is in principle possible to use any type of dyes or sensitizer, including combinations of different types of dyes or different dyes of the same type.

According to an embodiment, the sensitizer layer of the photovoltaic solid state device of the invention is coated by a layer comprising a compound of formula (I) and/or a compound according to any one of formulae (II) to (VI) or a combination thereof. Preferably said sensitizer layer comprises an organic-inorganic perovskite.

According to an embodiment, the sensitizer or the sensitizer layer comprises, consists of or is made of an organic-inorganic perovskite. Said organic-inorganic perovskite is provided under a film of one perovskite pigment or mixed perovskite pigments or perovskite pigments mixed with further dyes or sensitizers.

According to a further embodiment, the sensitizer layer comprises a further pigment in addition to the organic-inorganic perovskite pigment, said further pigment selected from organic pigment, organometallic pigment or inorganic pigment.

According to another embodiment, the optoelectronic and/or photoelectrochemical device of the invention is a dye sensitized solar cell (DSC) comprising a compound of formula (I) or of formula (II) to (VI) as hole transporting material and a pigment as sensitizer selected from organic pigment organometallic pigment or inorganic pigment or a combination thereof, as defined below.

Organometallic sensitizers (dye or pigment) are disclosed, for example, in EP0613466, EP0758337, EP0983282, EP1622178, WO 2006/038823, WO 2009/107100, WO 2010/055471, WO 2011/039715 and porphyrin based compounds in PCT/IB2014/066581 and in European patent application no. EP13197269.7. Exemplary organic dyes (or pigment) are those disclosed in WO2009/098643, EP1990373, WO 2007/100033 for example. An organic dye was also used in European patent application no. EP 111161954.0, and in PCT/IB2011/054628. Metal free organic sensitizers (pigment or dye) such as DPP based compounds are disclosed in PCT/IB2013/056648 and in European patent application no. EP12182817.2.

The term "perovskite", for the purpose of this specification, refers to the "perovskite structure" and not specifically to the perovskite material, CaTiO3. For the purpose of this specification, "perovskite" encompasses and preferably relates to any material that has the same type of crystal structure as calcium titanium oxide and of materials in which the bivalent cation is replaced by two separate monovalent cations. The perovskite structure has the general stoichiometry $AMX_3$, where "A" and "M" are cations and "X" is an anion. The "A" and "M" cations can have a variety of charges and in the original Perovskite mineral ($CaTiO_3$), the A cation is divalent and the M cation is tetravalent. For the purpose of this invention, the perovskite formulae includes structures having three (3) or four (4) anions, which may be the same or different, and/or one or two (2) organic cations, and/or metal atoms carrying two or three positive charges, in accordance with the formulae presented elsewhere in this specification.

According to an embodiment, the photovoltaic device of the invention comprises one or more layer of an organic-inorganic perovskite.

According to an embodiment, the sensitizer layer comprises, consists essentially of or consists of a nanocomposite material or an organic-inorganic pigments. According to a preferred embodiment, the sensitizer layer comprises, consists essentially of or consists of an organic-inorganic perovskite.

In a further embodiment of the optoelectronic and/or photoelectrochemical device of the invention, the organic-inorganic perovskite layer material comprises a perovskite-structure of any one of formulae (VII), (VIII), (IX), (X), (XI) and/or (XII) below:

$$AA'MX_4 \quad (VII)$$

$$AMX_3 \quad (VIII)$$

$$AA'N_{2/3}X_4 \quad (IX)$$

$$AN_{2/3}X_3 \quad (X)$$

$$BN_{2/3}X_4 \quad (XI)$$

$$BMX_4 \quad (XII),$$

wherein
- A and A' are organic, monovalent cations that are independently selected from primary, secondary, tertiary or quaternary organic ammonium compounds, including N-containing heterorings and ring systems, A and A' having independently from 1 to 60 carbons and 1 to 20 heteroatoms;
- B is an organic, bivalent cation selected from primary, secondary, tertiary or quaternary organic ammonium, compounds having from 1 to 60 carbons and 2-20 heteroatoms and having two positively charged nitrogen atoms;
- M is a divalent metal cation selected from the group consisting of $Cu^{2+}$, $Ni^{2+}$, $Co^{2+}$, $Fe^{2+}$, $Mn^{2+}$, $Cr^{2+}$, $Pd^{2+}$, $Cd^{2+}$, $Ge^{2+}$, $Sn^{2+}$, $Pb^{2+}$, $Eu^{2+}$, or $Yb^{2+}$;
- N is selected from the group of $Bi^{3+}$ and $Sb^{3+}$; and,
- X is independently selected from $Cl^-$, $Br^-$, $I^-$, $NCS^-$, $CN^-$, and $NCO^-$.

In particular, the three or four X may be the same or different. For example, in $AMX_3$ (formula VIII) may be expressed as formula (VIII') below:

$$AMXiXiiXiii \quad (VIII')$$

wherein Xi, Xii, Xiii are independently selected from $Cl^-$, $Br^-$, $I^-$, $NCS^-$, $CN^-$, and $NCO^-$, preferably from halides ($Cl^-$, $Br^-$, $I^-$), and A and M are as defined elsewhere in this specification. Xi, Xii, Xiii may thus be the same or different in this case. The same principle applies to the perovskites of formulae (VII) and (IX)-(XIII) and the more specific embodiments of formulae (XIV) to (XX) below. In case of $AA'MX_4$ (formula VII); for example, formula (VII') applies:

$$AA'MXiXiiXiiiXiv \quad (VII')$$

wherein Xi, Xii, Xiii are independently selected from $Cl^-$, $Br^-$, $I^-$, $NCS^-$, $CN^-$, and $NCO^-$, preferably form halides ($Cl^-$, $Br^-$, $I^-$).

Preferably, if Xi, Xii, Xiii in formulae (VIII) and (X) or Xi, Xii, Xiii, Xiv in formulae (VII), (IX), (XI) or (XII) comprise different anions X, there are not more than two different anions.

For example, Xi and Xii being the same with Xiii being an anion that is different from Xi and Xii.

According to a preferred embodiment, the perovskite material has the structure selected from one or more of formulae (VII) to (IX), preferably (VIII) or (VIII').

According to a preferred embodiment, said organic-inorganic perovskite layer comprises a perovskite-structure of any one of the formulae (XIV) to (XX):

$$APbX_3 \quad (XIV)$$

$$ASnX_3 \quad (XIV)$$

$$ABiX_4 \quad (XVI)$$

$$AA'PbX_4 \quad (XVII)$$

$$AA'SnX_4 \quad (XVIII)$$

$$BPbX_4 \quad (XIX)$$

$$BSnX_4 \quad (XX)$$

wherein A, A', B and X are as defined elsewhere in this specification. Preferably, X is preferably selected from $Cl^-$, $Br^-$, and $I^-$, most preferably X is $I^-$.

According to a preferred embodiment, said organic-inorganic perovskite layer comprises a perovskite-structure of the formulae (XIV) to (XVIII), more preferably (XIV) and/or (XV) above.

According to an embodiment, A and A' are monovalent cations selected independently from any one of the compounds of formulae (41) to (48) below:

(41)

(42)

(43)

(44)

(45)

(46)

(47)

(48)

wherein,
any one of $R^{48}$, $R^{49}$, $R^{50}$ and $R^{51}$ is independently selected from C1-C15 organic substituents comprising from 0 to 15 heteroatoms.

According to an embodiment of said C1-C15 organic substituent any one, several or all hydrogens in said substituent may be replaced by halogen and said organic substituent may comprise up to fifteen (15) N, S or O heteroatoms, and wherein, in any one of the compounds (41) to (48), the two or more of substituents present ($R^{48}$, $R^{49}$, $R^{50}$ and $R^{51}$, as applicable) may be covalently connected to each other to form a substituted or unsubstituted ring or ring system. Preferably, in a chain of atoms of said C1-C15 organic substituent, any heteroatom is connected to at least one carbon atom. Preferably, neighboring heteroatoms are absent and/or heteroatom-heteroatom bonds are absent in said C1-C15 organic substituent comprising from 0 to 15 heteroatoms. The heteroatoms may be selected from N, S, and/or O.

According to an embodiment any one of $R^{48}$, $R^{49}$, $R^{50}$ and $R^{51}$ is independently selected from C1 to C15 aliphatic and C4 to C15 aromatic or heteroaromatic substituents, wherein any one, several or all hydrogens in said substituent may be replaced by halogen and wherein, in any one of the compounds (41) to (48), the two or more of the substituents present may be covalently connected to each other to form a substituted or unsubstituted ring or ring system.

According to an embodiment, B is a bivalent cation selected from any one of the compounds of formulae (49) and (50) below:

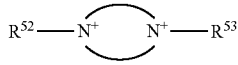     (49)

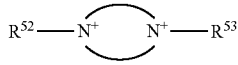     (50)

wherein, in the compound of formula (49), G is an organic linker structure having 1 to 10 carbons and 0 to 5 heteroatoms selected from N, S, and/or O, wherein one or more hydrogen atoms in said G may be replaced by halogen;

wherein any one of $R_{48}$ and $R_{49}$ is independently selected from any one of the substituents (51) to (56) below:

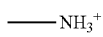     (51)

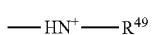     (52)

     (53)

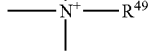     (54)

     (55)

     (56)

wherein the dotted line in the substituents (51) to (56) represents the bond by which said substituent is connected to the linker structure G;

wherein $R^{48}$, and $R^{49}$, and $R^{50}$ are independently as defined above with respect to the compounds of formulae (41) to (48);

wherein $R_{48}$ and $R_{49}$, if they are both different from substituent (51), may be covalently connected to each other by way of their substituents $R^{48}$, $R^{49}$, and/or $R^{50}$, as applicable, and wherein any one of $R^{48}$, $R^{49}$, and $R^{50}$, if present, may be covalently connected to G or the ring structure of compound (49), independently from whether said substituent is present on $R_{48}$ or $R^{49}$;

and wherein, in the compound of formula (50), the circle containing said two positively charged nitrogen atoms represents a substituted or unsubstituted aromatic ring or ring system comprising 4 to 15 carbon atoms and 2 to 7 heteroatoms or 4 to 10 carbon atoms and 2 to 5 heteroatoms, wherein said nitrogen atoms are ring heteroatoms of said ring or ring system, and wherein the remaining of said heteroatoms may be selected independently from N, O and S and wherein $R^{52}$ and $R^{53}$ are independently selected from H and from substituents as $R^{48}$ to $R^{51}$. Halogen atom substituting hydrogen atom totally or partially may also be present in addition to and/or independently of said 2 to 7 heteroatoms.

Preferably, if the number of carbons is in G is impair, the number of heteroatoms is smaller than the number of carbons. Preferably, in the ring structure of formula (50), the number of ring heteroatoms is smaller than the number of carbon atoms. According to an embodiment, G is an aliphatic, aromatic or heteroaromatic linker structure having from 1 to 10 carbons.

Preferably, the dotted line in substituents (51) to (56) represents a carbon-nitrogen bond, connecting the nitrogen atom shown in the substituent to a carbon atom of the linker.

According to an embodiment, in the compound of formula (49), G is an organic linker structure having 1 to 8 carbons and from 0 to 4 N, S and/or O heteroatoms of having 1 to 6 carbons and from 0 to 3 N, S and/or O heteroatoms, wherein any one, several or all hydrogens in said G may be replaced by halogen. Preferably, L is an aliphatic, aromatic or heteroaromatic linker structure having 1 to 8 carbons, wherein any one, several or all hydrogens in said G may be replaced by halogen. According to an embodiment, in the compound of formula (49), said linker G is free of any O or S heteroatoms. According to an embodiment, G is free of N, O and/or S heteroatoms.

According to an embodiment, any one of $R^{48}$, $R^{49}$, $R^{50}$ and $R^{51}$ is independently selected from C1 to C10 alkyl, C2 to C10 alkenyl, C2 to C10 alkynyl, C4 to C10 heteroaryl and C6 to C10 aryl, wherein said alkyl, alkenyl, and alkynyl, if they comprise 3 or more carbons, may be linear, branched or cyclic, wherein said heteroaryl and aryl may be substituted or unsubstituted, and wherein several or all hydrogens in $R^{48}$-$R^{51}$ may be replaced by halogen.

According to an embodiment, any one of $R^{48}$, $R^{49}$, $R^{50}$ and $R^{51}$ is independently selected from C1 to C8 alkyl, C2 to C8 alkenyl, C2 to C8 alkynyl, C4 to C8 heteroaryl and C6 to C8 aryl, wherein said alkyl, alkenyl, and alkynyl, if they comprise 3 or more carbons, may be linear, branched or cyclic, wherein said heteroaryl and aryl may he substituted or unsubstituted, and wherein several or all hydrogens in $R^{48}$-$R^{51}$ may be replaced by halogen.

According to an embodiment, any one of $R^{48}$, $R^{49}$, $R^{50}$ and $R^{51}$ is independently selected from C1 to C6 alkyl, C2 to C6 alkenyl, C2 to C6 alkynyl, C4 to C6 heteroaryl and C6 aryl, wherein said alkyl, alkenyl, and alkynyl, if they comprise 3 or more carbons, may be linear, branched or cyclic, wherein said heteroaryl and aryl may be substituted or unsubstituted, and wherein several or all hydrogens in $R^{48}$-$R^{51}$ may be replaced by halogen.

According to an embodiment, any one of $R^{48}$, $R^{49}$, $R^{50}$ and $R^{51}$ is independently selected from C1 to C4 alkyl, C2 to C4 alkenyl and C2 to C4 alkynyl, wherein said alkyl, alkenyl and alkynyl, if they comprise 3 or more carbons, may be linear, branched or cyclic, and wherein several or all hydrogens in $R^{48}$-$R^{51}$ may be replaced by halogen.

According to an embodiment, any one of $R^{48}$, $R^{49}$, $R^{50}$ and $R^{51}$ is independently selected from C1 to C3, preferably C1 to C2 alkyl, C2 to C3, preferably C2 alkenyl and C2 to C3, preferably C2 alkynyl, wherein said alkyl, alkenyl and alkynyl, if they comprise 3 or more carbons, may be linear, branched, or cyclic, and wherein several or all hydrogens in $R^{48}$-$R^{51}$ may be replaced by halogen.

According to an embodiment, any one of $R^{48}$, $R^{49}$, $R^{50}$ and $R^{51}$ is independently selected from C1 to C4, more preferably C1 to C3 and even more preferably C1 to C2 alkyl. Most preferably, any one of $R^{48}$, $R^{49}$, $R^{50}$ and $R^{51}$ are methyl. Again, said alkyl may be completely or partially halogenated.

According to an embodiment, A, A' and B are monovalent (A, A') and bivalent (B) cations, respectively, selected from substituted and unsubstituted C5 to C6 rings comprising one, two or more nitrogen heteroatoms, wherein one (for A and A') or two (for B) of said nitrogen atoms is/are positively charged. Substituents of such rings may be selected from halogen and from C1 to C4 alkyls, C2 to C4 alkenyls and C2 to C4 alkynyls as defined above, preferably from C1 to C3 alkyls, C3 alkenyls and C3 alkynyls as defined above. Said ring may comprise further heteroatoms, which may be selected from O, N and S. Bivalent organic cations B comprising two positively charged ring N-atoms are exemplified, for example, by the compound of formula (50) above. Such rings may be aromatic or aliphatic.

A, A' and B may also comprise a ring system comprising two or more rings, at least one of which being from substituted and unsubstituted C5 to C6 ring as defined as above. The elliptically drawn circle in the compound of formulae (50) may also represent a ring system comprising, for example, two or more rings, but preferably two rings. Also if A and/or A' comprises two rings, further ring heteroatoms may be present, which are preferably not charged, for example.

According to an embodiment, however, the organic cations A, A' and B comprise one (for A, A'), two (for B) or more nitrogen atoms(s) but are free of any O or S or any other heteroatom, with the exception of halogens, which may substitute one or more hydrogen atoms in cation A and/or B.

A and A' preferably comprise one positively charged nitrogen atom, B preferably comprises two positively charged nitrogen atoms.

A, A' and B may be selected from the exemplary rings or ring systems of formulae (57) and (58) (for A) and from (59) to (61) (for B) below:

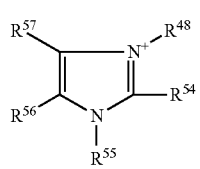

(57)

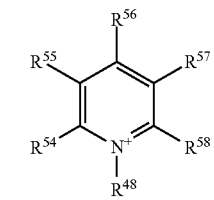

(58)

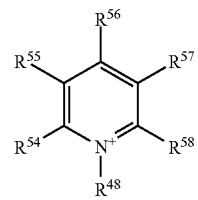

(59)

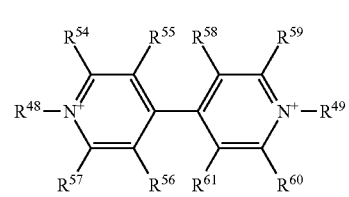

(60)

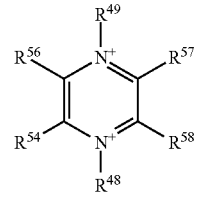

(61)

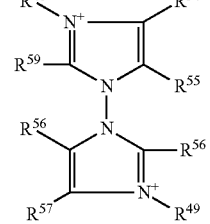

in which $R^{48}$ and $R^{49}$ are, independently, as defined above, and $R^{54}$, $R^{55}$, $R^{56}$, $R^{57}$, $R^{58}$, $R^{59}$ and $R^{60}$ are independently selected from H, halogen and substituents as defined above for $R^{48}$ to $R^{51}$. Preferably, $R^{54}$, $R^{55}$, $R^{56}$, $R^{57}$, $R^{58}$, $R^{59}$ and $R^{60}$ are selected from H and halogen, most preferably H.

In the organic cations A, A' and B, hydrogen atoms may be substituted by halogens, such as F, Cl, I, and Br, preferably F or Cl. Such a substitution is expected to reduce the hygroscopic properties of the perovskite layer or layers and may thus provide a useful option for the purpose of the present specification.

According to a preferred embodiment, A and A' are independently selected from organic cations of formula (41). Preferably, $R^{48}$ in the cation of formula (41) is selected from C1 to C8 organic substituents comprising, from 0 to 4 N, S and/or O heteroatom. More preferably, $R^1$ is selected from C1 to C4, preferably C1 to C3 and most preferably C1 to C2 aliphatic substituents.

According to a preferred embodiment, the metal M is selected from $Sn^{2+}$ and $Pb^{2+}$, preferably $Pb^{2+}$. According to a preferred embodiment, N is $Sb^{3+}$.

According to a preferred embodiment, the three or four X are independently selected from $Cl^-$, $Br^-$, and $I^-$.

According to a preferred embodiment, the organic-inorganic perovskite material has the formula of formulae (XXI) to (XXV) below:

$AMI_3$ (XXI)

$AMI_2Br$ (XXII)

$AMI_2Cl$ (XXIII)

AMBr₃ (XXIV)

AMCl₃ (XXV)

wherein A and M are as defined elsewhere in this specification, including the preferred embodiments of A and M, such as those defined below. Preferably, M is selected from $Sn^{2+}$ and $Pb^{2+}$. Preferably, A is selected from organic cations of formula (41). Preferably, $R^{48}$ in the cation of formula (41) is selected from C1 to C8 organic substituents comprising, from 0 to 4 N, S and/or O heteroatom. More preferably, $R^{48}$ is selected from C1 to C4, preferably C1 to C3 and most preferably C1 to C2 aliphatic substituents.

According to a preferred embodiment, the organic-inorganic perovskite is a compound of formula (XIII) (AMXiXiiXiii), wherein A is a monovalent cation of formula (41) as defined above, M is $Sn^{2+}$ or $Pb^{2+}$, and Xi, Xii, Xiii are independently selected from $Cl^-$, $Br^-$, $I^-$. Preferably, $R^{48}$ in the cation of formula (41) is selected from C1 to C4, preferably C1 to C3 and most preferably C1 to C2 aliphatic substituents. Preferably, Xi-Xiii are identical.

In a further aspect, the invention provides a use of a compound of formula (I) and/or according to any one of formulae (II) to (VI) as a hole transporting material in optoelectronic or photoelectrochemical device.

The present invention will now be illustrated by way of examples. These examples do not limit the scope of this invention, which is defined by the appended claims.

EXAMPLES

Example 1

Synthesis of the Compounds of the Invention Based on Diphenylamine Substituted Carbazole and In Particular Compounds (21)-(26)

The synthesis route to these hole transporting materials involves the click reaction of suitable bis(bromomethyl) benzene with 3,6-dibromocarbazole, followed by the palladium catalyzed C-N cross-coupling reaction with diphenylamine derivatives (see FIG. 1).

1,2-Bis(3,6-dibromo-9H-carbazol-9-methyl)benzene (see FIG. 1, Intermediate Compound 1a).

A mixture of 3,6-dibromo-9H-carbazole (1.30 g, 4 mmol) and 1,2-bis(bromomethyl)benzene (0.53 g, 2 mmol) was dissolved in 15 ml of THF and 0.80 g (0.012 mol) of 85% powdered potassium hydroxide was added in small portions during 2-3 minutes. The obtained mixture was vigorously stirred at room temperature for 10 min (TCL, acetone: hexane, 1:4). White crystals of intermediate compound 1a (1.35 g, 89.7%) formed were filtered off and washed with water until neutral and three times with ethanol. The produce was dried in vacuum oven at 40° C. for 24 hours and used in the next step without additional purification.

M.p.=317-319° C. ¹H NMR (700 MHz, DMSO-d₆), ppm: 8.60 (s, 4H), 7.67 (t, J=5.8 Hz, 8H), 6.90 (dd, J=5.6, 3.2 Hz, 2H), 6.00 (s, 4H), 5.97-5.94 (m, 2H), ¹³C NMR (176 MHz, DMSO-d₆), ppm: 139.52, 133.99, 129.07, 127.00, 123.86, 123.74, 123.18, 112.07, 111.91, 43.23.

1,3-Bis(3,6-dibromo-9H-carbazol-9-methyl)benzene (See FIG. 1, Intermediate Compound 1b).

A mixture of 3,6-dibromo-9H-carbazole (1.30 g, 4 mmol) and 1,3-bis(bromomethyl)benzene (0.53 g, 2 mmol) was dissolved in 15 ml of THF and 0.80 g (0.012 mol) of 85% powdered potassium hydroxide was added in small portions during 2-3 minutes. The obtained mixture was vigorously stirred at room temperature for 10 min (TCL, acetone: hexane, 1:4). White crystals of intermediate compound 1b (1.3 g, 86%) formed were filtered off and washed with water until neutral and three times with ethanol. The product was dried in vacuum oven at 40° C. for 24 hours and used in the next step without additional purification.

M.p.=255-256° C., ¹H NMR (700 MHz, DMSO-d₆), ppm: 8.41 (d, J=1.9 Hz, 4H), 7.45 (dd, J=8.7, 2.0 Hz, 4H), 7.40 (d, J=8.7 Hz, 4H), 7.18 (t, J=7.7 Hz, 1H), 7.03 (dd, J=7.7, 1.0 Hz, 2H), 6.63 (s, 1H), 5.52 (s, 4H). ¹³C NMR (176 MHz, DMSO-d₆), ppm: 138.98, 137.56, 128.95, 128.76, 125.85, 124.64, 123.36, 122.95, 111.63, 111.54, 45.47.

1,4-Bis(3,6-dibromo-9H-carbazol-9-methyl)benzene (See FIG. 1, Intermediate Compound 1c).

A mixture of 3,6-dibromo-9H-carbazole (1.30 g, 4 mmol) and 1,4-bis(bromomethyl)benzene (0.53 g, 2 mmol) was dissolved in 15 ml of THF and 0.80 g (0.012 mol) of 85% powdered potassium hydroxide was added in small portions during 2-3 minutes. The obtained mixture was vigorously stirred at room temperature for 10 min (TCL, acetone: hexane, 1:4). White crystals of intermediate compound 1c (1.37 g, 91.1%) formed were filtered off and washed with water until neutral and three times with ethanol. The produce was dried in vacuum oven at 40° C. for 24 hours and used in the next step without additional purification.

M.p.=330-332° C. ¹H NMR (700 MHz, DMSO-d₆), ppm: 8.48 (d, J=1.4 Hz, 4H), 7.59-7.54 (m, 8H), 7.01 (s, 4H), 5.60 (s, 4H). ¹³C NMR (176 MHz, DMSO-d₆), ppm: 139.16, 136.40, 128.98, 126.92, 123.52, 123.09, 111.86, 111.63, 45.39.

1,2-Bis[3,6-(4,4-dimethyldiphenylamino)-9H-carbazol-9-methyl]benzene (See FIG. 1, Compound 2a or V-931 or Compound (22)).

A solution of intermediate compound 1a (1.13 g, 1.5 mmol), 4,4'-dimethyldiphenylamine (1.48 g, 7.5 mmol) in anhydrous toluene (15 mL) was purged with argon for 20 minutes. Afterward, palladium(II) acetate (6.7 mg, 0.03 mmol), tri-tert-butylphosphonium tetrafluoroborate (11.6 mg, 0.04 mmol) and sodium tert-butoxide (0.72 g, 7.5 mmol) were added and the solution was refluxed under argon atmosphere for 20 hours. After cooling to room temperature, reaction mixture was filtered through Celite, 50 mL or distilled water was added to the filtrate and extraction was done with ethyl acetate. The combined organic layer was dried over anhydrous $Na_2SO_4$, filtered and solvent evaporated. The crude product was purified by column chromatography using 1:3 v/v acetone/n-hexane as an eluent. The obtained produce was precipitated from 20% solution in acetone into 15-fold excess of methanol. The precipitate was filtered off and washed with methanol to collect final compound 2a as a pale yellow solid (1.27 g, 69%).

¹H NMR (700 MHz, DMSO-d₆) δ 7.64-6.81 (m, 48H), 5.98 (s, 4H), 2.18 (s, 24H). ¹³C NMR (176 MHz, DMSO-d₆) δ 151.46, 139.19, 129.71, 129.51, 128.03, 125.86, 124.91, 122.25, 122.10, 120.47, 119.23, 116.68, 109.69, 43.08, 20.24. Anal. calcd for $C_{88}H_{76}N_6$: C, 86.81; H, 6.29; N, 6.90; found: C, 86.69; H, 6.23; N, 6.85.

1,3-Bis[3,6-(4,4-dimethyldiphenylamino)-9H-carbazol-9-methyl]benzene (See FIG. 1, Compound 2b or V-928 or Compound (24)).

A solution of intermediate compound 1b (1.13 g, 1.5 mmol), 4,4'-dimethyldiphenylamine (1.48 g, 7.5 mmol) in anhydrous toluene (15 ml) was purged with argon for 20 minutes. Afterwards, palladium(II) acetate (6.7 mg, 0.03 mmol), tri-tert-butylphosphonium tetrafluoroborate (11.5 mg, 0.04 mmol) and sodium tert-butoxide (0.72 g, 7.5 mmol) were added and the solution was refluxed under argon atmosphere for 20 hours. After cooling to mom temperature, reaction mixture was filtered through Celite. 50 mL of distilled water was added to the filtrate and extraction was done with ethyl acetate. The combined organic layer was dried over anhydrous $Na_2SO_4$, filtered and solvent evaporated. The crude product was purified by column chromatography using 1:3 v/v acetone/n-hexane as an eluent. The obtained product was precipitated from 20% solution in acetone into 15-fold excess of methanol. The precipitate was filtered off and washed with methanol to collect final compound 2b as a pale yellow solid (1.42 g, 78%). $^1$H NMR (700 MHz, DMSO-$d_6$) δ 7.77 (s, 4H), 7.53 (d, J=8.4 Hz, 4H), 7.46 (s, 1H), 7.29-7.17 (m, 3H), 7.07-6.95 (m, 20H), 6.78 (d, J=7.7 Hz, 16H), 5.53 (s, 4H), 2.19 (s, 16H). $^{13}$C NMR (176 MHz, DMSO-$d_6$) δ 145.92, 139.44, 137.64, 132.08, 130.20, 129.64, 129.45, 126.72, 126.47, 125.44, 122.88, 122.02, 118.32, 110.68, 45.90, 20.23. Anal. calcd for $C_{88}H_{76}N_6$: C, 86.81; H, 6.29; N, 6.90; found: C, 86.72; H, 6.28; N, 6.88.

1,4-Bis[3,6-(4,4-dimethyldiphenylamino)-9H-carbazol-9-methyl]benzene (See FIG. 1, Compound 2c or V-908 or Compound (26)).

A solution of intermediate compound 1c (1.13 g, 1.5 mmol), 4,4'-dimethyldiphenylamine (1.48 g, 7.5 mmol) in anhydrous toluene (15 mL) was purged with argon for 20 minutes. Afterwards, palladium(II) acetate (6.7 mg, 0.03 mmol), tri-tert-butylphosphonium tetrafluoroborate (11.5 mg, 0.04 mmol) and sodium tert-butoxide (0.72 g, 7.5 mmol) were added and the solution was refluxed under argon atmosphere for 20 hours. After cooling to room temperature, reaction mixture was filtered through Celite. 50 mL of distilled water was added to the filtrate and extraction was done with ethyl acetate. The combined organic layer was dried over anhydrous $Na_2SO_4$, filtered and solvent evaporated. The crude product was purified by column chromatography using 1:3 v/v acetone/n-hexane as an eluent. The obtained product was precipitated from 20% solution in acetone into 15-fold excess of methanol. The precipitate was filtered off and washed with methanol to collect final compound 2c as a pale yellow solid (1.26 g, 69%).

$^1$H NMR (700 MHz, DMSO-$d_6$), ppm: 7.75 (s, 4H), 7.45 (s, 4H), 7.17-6.70 (m, 40H), 5.48 (s, 4H), 2.18 (s, 24H). $^{13}$C NMR (176 MHz, DMSO-$d_6$), ppm: 145.91, 139.45, 137.68, 136.86, 130.18, 129.62, 127.08, 125.40, 122.85, 122.03, 118.29, 110.52, 45.49, 20.22. Anal. calcd for $C_{88}H_{76}N_6$: C, 86.81; H, 6.29; N, 6.90; found: C, 86.67; H, 6.21; N, 6.86.

1,2-Bis[3,6-(4,4-dimethoxydiphenylamino)-9H-carbazol-9-methyl]benzene (See FIG. 1, Compound 2d or V-886 or Compound (21)).

A solution of intermediate compound 1a (1.13 g, 1.5 mmol), 4,4'-dimethoxydiphenylamine (1.72 g, 7.5 mmol) in anhydrous toluene (15 mL) was purged with argon for 20 minutes.

Afterward, palladium(II) acetate (6.7 mg, 0.03 mmol), tri-tert-butylphosphonium tetrafluoroborate (11.5 mg, 0.04 mmol) and sodium tert-butoxide (0.72 g, 7.5 mmol) were added and the solution was refluxed under argon atmosphere for 20 hours. After cooling to room temperature, reaction mixture was filtered through Celite. 50 mL of distilled water was added to the filtrate and extraction was done with ethyl acetate. The combined organic layer was dried over anhydrous $Na_2SO_4$, filtered and solvent evaporated. The crude product was purified by column chromatography using 1:3 v/v acetone-n-hexane as an eluent. The obtained product was precipitated from 20% solution in acetone into 15-fold excess of methanol. The precipitate was filtered off and washed with methanol to collect compound 2d as a pale yellow solid (1.35 g, 67%).

$^1$H NMR (700 MHz, DMSO-$d_6$), ppm: 7.71 (d, J=1.5 Hz, 4H), 7.39 (d, J=8.8 Hz, 4H), 7.08 (dd, J=8.7, 1.4 Hz, 4H), 7.02 (dd, J=5.1, 3.4 Hz, 2H), 6.85 (d, J=8.9 Hz, 16H), 6.78 (d, J=9.0 Hz, 16H), 6.48-6.44 (m, 2H), 5.80 (s, 4H), 3.66 (s, 24H). $^{13}$C NMR (176 MHz, DMSO-$d_6$), ppm: 154.23, 142.01, 140.48, 137.47, 132.72, 129.43, 124.30, 123.81, 122.88, 116.74, 114.63, 113.83, 110.53, 55.13, 43.53. Anal. calcd for $C_{88}H_{76}N_6O_8$: C, 78.55; H, 5.69; N, 6.25; found: C, 78.50; H, 5.66; N, 6.22.

1,3-Bis[3,6-(4,4-dimethoxydiphenylamino)-9H-carbazol-9-methyl]benzene (See FIG. 1, Compound 2e or V-885 or Compound (23)).

A solution of intermediate compound 1b (1.13 g, 1.5 mmol), 4,440-dimethoxydiphenylamine (1.72 g, 7.5 mmol) in anhydrous toluene (15 mL) was purged with argon for 20 minutes. Afterwards, palladium(II) acetate (6.7 mg, 0.03 mmol), tri-tert-butylphosphonium tetrafluoroborate (11.5 mg, 0.04 mmol) and sodium tert-butoxide (0.72 g, 7.5 mmol) were added and the solution was refluxed under argon atmosphere for 20 hours. After cooling to room temperature, reaction mixture was filtered through Celite. 50 mL of distilled water was added to the filtrate and extraction was done with ethyl acetate. The combined organic layer was dried over anhydrous $Na_2SO_4$, filtered and solvent evaporated. The crude product was purified by column chromatography using 1:3 v/v acetone/n-hexane as an eluent. The obtained product was precipitated from 20% solution in acetone into 15-fold excess of methanol. The precipitate was filtered off and washed with methanol to collect compound 2e as a pale yellow solid (1.75 g, 87%).

$^1$H NMR (700 MHz, DMSO-$d_6$), ppm: 7.66 (d, J=1.8 Hz, 4H), 7.50 (d, J=8.8 Hz, 4H), 7.46 (s, 1H), 7.23 (t, J=7.6 Hz, 1H), 7.14 (d, J=7.6 Hz, 2H), 7.04 (dd, J=8.7, 1.9 Hz, 4H), 6.84 (d, J=9.0 Hz, 16H), 6.78 (d, J=9.0 Hz, 16H), 5.51 (s, 4H), 5.51 (s, 4H), 3.68 (s, 24H). $^{13}$C NMR (176 MHz, DMSO-$d_6$), ppm; 154.27, 142.03, 140.24, 138.21, 137.15, 129.04, 126.76, 126.30, 124.37, 123.72, 122.76, 116.73, 114.60, 110.54, 55.07, 45.86. Anal. calcd for $C_{88}H_{76}N_6O_8$: C, 78.55; H, 5.69; N, 6.25; found: C, 78.48; H, 5.67; N, 6.21.

1,4-Bis[3,6-(4,4-dimethoxydiphenylamino)-9H-carbazol-9-methyl]benzene (see FIG. 1, Compound 2f or V-911 or Compound (25)).

A solution of intermediate compound 1c (1.13 g, 1.5 mmol), 4,4'-dimethoxydiphenylamine (1.72 g, 7.5 mmol) in anhydrous toluene (15 mL) was purged with argon for 20 minutes. Afterwards, Palladium(II) acetate (6.7 mg, 0.03 mmol), tri-tert-butylphosphonium tetrafluoroborate (11.5 mg, 0.04 mmol) and sodium tert-butoxide (0.72 g, 7.5 mmol) were added and the solution was refluxed under argon atmosphere for 20 hours. After cooling to room temperature, reaction mixture was filtered through Celite. 50 mL of distilled water was added to the filtrate and extraction was done with ethyl acetate. The combined organic layer was dried over anhydrous $Na_2SO_4$, filtered and solvent evaporated. The crude product was purified by column chromatography using 1:3 v/v acetone/n-hexane as an eluent. The obtained product was precipitated from 20% solution in acetone into 15-fold excess of methanol. The precipitate was filtered off and washed with methanol to collect compound 2f as a pale yellow solid (1.33 g, 66%).

$^1$H NMR (700 MHz, DMSO-$d_6$), ppm: 7.56 (s, 4H), 7.27 (s, 4H), 7.00-6.90 (m, 8H), 6.76 (d, J=8.9 Hz, 16H), 6.70 (d, J=9.0 Hz, 16H), 5.35 (s, 4H), 3.62 (s, 24H). $^{13}$C NMR (176 MHz, DMSO-$3_6$), ppm: 154.61, 142.50, 140.72, 137.64, 137.25, 127.38, 124.80, 124.22, 123.19, 117,15, 115.03, 110.73, 55.57, 45.89. Anal. calcd for $C_{88}H_{76}N_6O_8$: C, 78.55; H, 5.69; N, 6.25; found: C, 78.51; H, 5.62; N, 6.22.

Example 2

Photovoltaic Characterization of Compound of Formula (21) Corresponding to Compound V-886

Current Density—Voltage (J-V)

The performance of V-886 is tested in $CH_3NH_3PbI_3$-based solar cells using a mesoporous $TiO_2$ photo-anode and an Au cathode, following a procedure based on anti-solvent engineering developed by Seok in 2014 (Nam Joong Jeon et al., Nature Materials, 2014). The obtained device shows a maximum PCE of 15.1% under AM 1.5 G illuminations. The measured fill factor is 0.75, the current density ($J_{sc}$) 19.5 mA/cm$^2$ and the open-circuit voltage is found to be 1.02 V.

The high Jsc indicates that the photogenerated charge carriers are efficiently extracted and the high $V_{oc}$ reveals possibly good energy level alignment between perovskite valence band and the HOMO of V-886. This high $V_{oc}$ also indicates slow recombination between injected holes and electrons from either the perovskite capping layer or $TiO_2$.

Figure 5:
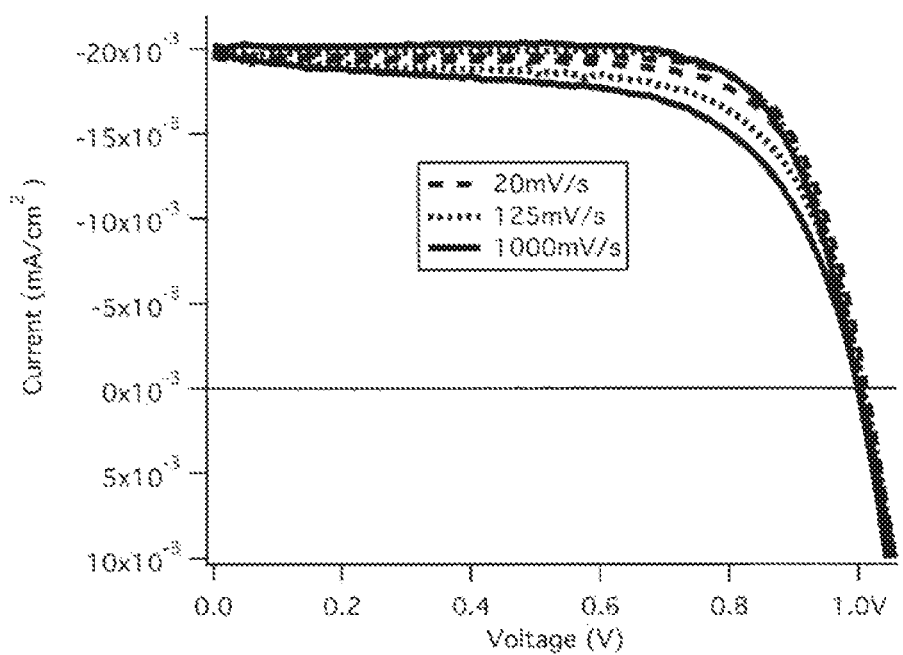
FIG. 5 shows curves of Current-Voltage. The hole mobility is determined to be $1.4E^{-5}$ cm2 $V^{-1}$ $s^{-1}$.

The hysteresis of the current-voltage curve decreases with decreasing scan speed is shown in FIG. 5. This typical behaviour is commonly observed in perovskite solar cells containing a mesoporous $TiO_2$ scaffold. According to a recent work by E. L. Unger (Unger et al., Energy & Env. Science, 2014, 7), either very fast or very slow scans lead to hysteresis-free light IV curves.

Absorbance

Figure 3:
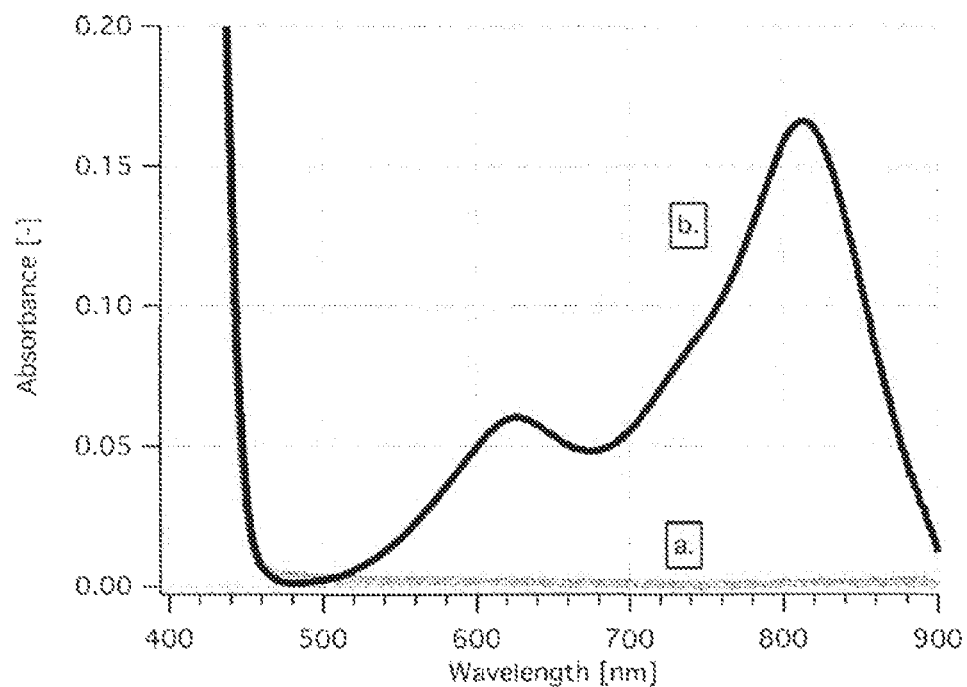
FIG. 3A shows UV-Visible absorbance spectrum of a solution of the reduced compound V-886 ((a), light grey line) and of the oxidized compound V-886 ((b), dark gray line).
FIG. 3B shows the absorbance of the compound V-886 in the Visible and Near-Infrared region.
Figure 3:
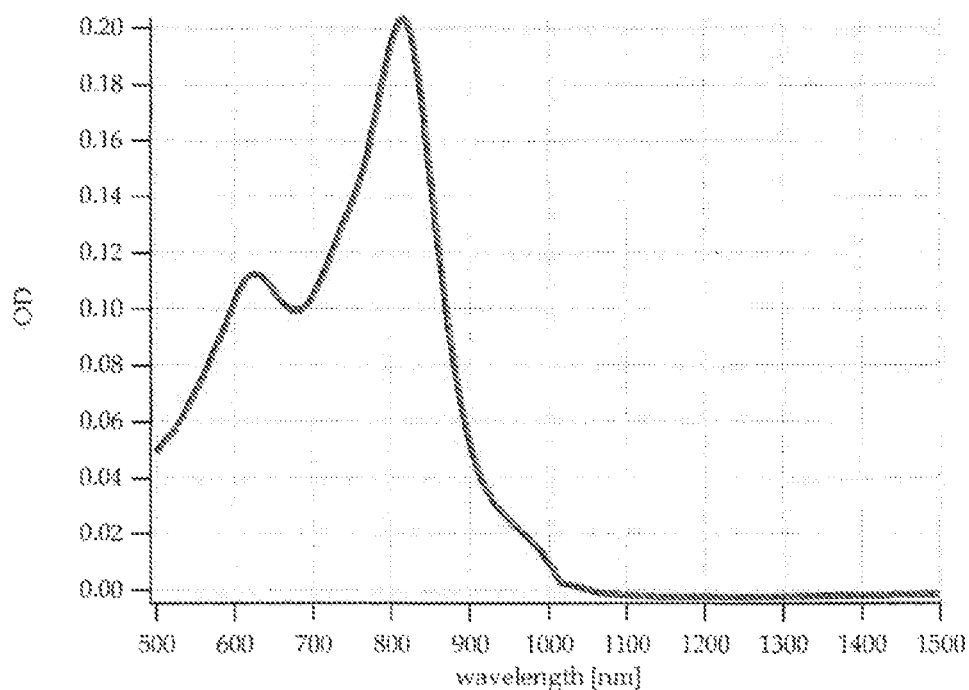

FIG. 3A shows the difference in absorbance upon chemical oxidation of V-886 by the Cobalt (II) complex FK209 (J. Burschka et al., J. Am. Chem. Soc., 2011, 133 (45)). In its pristine form, V-886 only absorbs mostly in the UV region below 450 nm. Chemically oxidized V-886 has a visible absorption bands at 628 nm and 814 nm, showing the formation of the oxidized species.

Since the $CH_3NH_3PbI_3$ perovskite absorption cuts off at 780 nm, the absorption of the oxidized V-886 at 823 nm does not compete with the perovskite. Additionally, oxidized V886 does not absorb in the infrared part of the spectrum, as shown in Figure (SI), making this hole conductor an interesting option for the semi-transparent devices that are part of a hybrid tandem architecture.

Conductivity/Mobility

Figure 4:
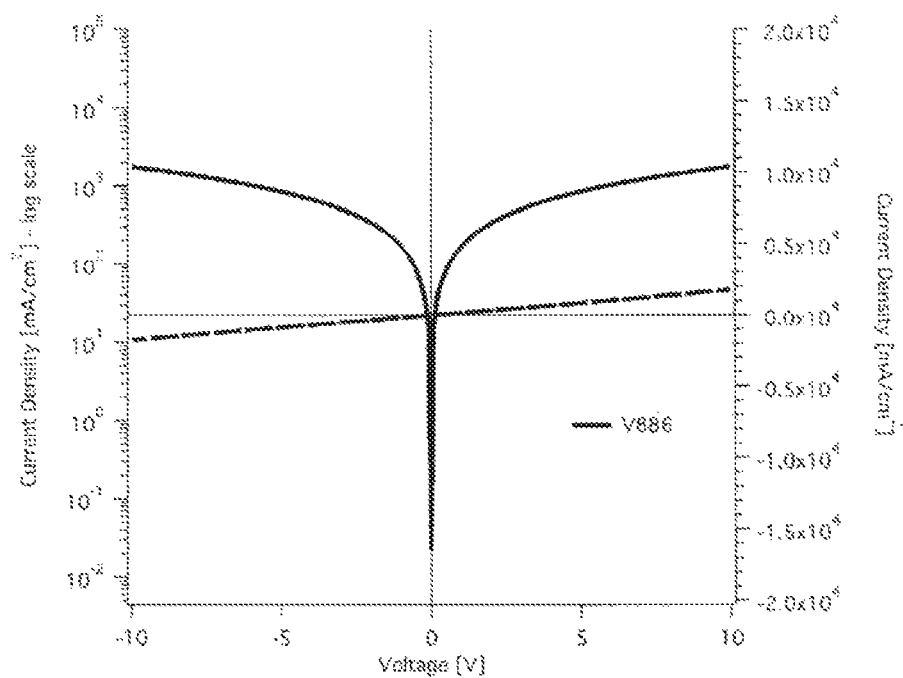
FIG. 4 shows Conductivity plot of a doped V-886 (line) thin film. Conductivity was extracted form a linear fit in the −5V to 5V region. Current-Voltage characteristics of Au/V-886/Au (OFET substrate). The conductivity is extracted from the slope of a linear fit using Ohm's law.

Lateral thin film conductivity has been measured by spin coating a film of chemically oxidized V-886 from chlorobenzene on OFET substrates (Fraunhofer Institute for Photonic Microsystems IPMS, 01109 Dresden, Germany). Without addition of FK209, no Ohmic contact could be observed and the measured currents are very small compared to the currents measured upon addition of FK209. In the case of oxidized V-886, Ohmic contacts are formed with gold and the conductivity upon addition of 10 mol % of FK209 is extracted by making a linear fit and using Ohm's law (FIG. 4). The conductivity of oxidized V-886 is determined to be $4.2 \times 10^{-5}$ S/cm, indicating that the chemical oxidation of V886 actually results in doping i.e. an increase of carrier concentration and hence conductivity.

Ionization Potential Measurements

The solid state ionization potential ($I_p$) of the layers of the compounds of formulae (21) to (26) was measured by the electron photoemission in air method. The samples for the ionization potential measurement were prepared by dissolving materials in $CHCl_3$ and were coated on Al plates pre-coated with ~0.5 μm methylmethacrylate and methacrylic acid copolymer adhesive layer. The thickness of the transporting material layer was $0.5^{-1}$ μm. Photoemission experiments are carried out in vacuum and high vacuum is one of the main requirements for these measurements. If vacuum is not high enough the sample surface oxidation and gas adsorption are influencing the measurement results. In our case, however, the organic materials investigated are stable enough to oxygen and the measurements may be carried out in the air. The samples were illuminated with monochromatic light from the quarts monochromator with deuterium lamp. The power of the incident light beam was (2-5) $10^{-8}$ W. The negative voltage of −300 V was supplied to the sample substrate. The counter-electrode with the 4.5×15 mm$^2$ slit for illumination was placed at 8 mm distance from the sample surface. The counter-electrode was connected to the input of the BK2-16 type electrometer, working in the open input regime, for the photocurrent measurement. The $10^{-15}$-$10^{-12}$ A strong photocurrent was flowing in the circuit under illumination. The photocurrent I is strongly dependent on the incident light photon energy hν. The $I^{0.5}=f(h\nu)$ dependence was plotted. Usually the dependence of the photocurrent on incident light quanta energy is well described by linear relationship between $I^{0.5}$ and hν near the threshold. The linear part of this dependence was extrapolated to the hν axis and $I_p$ value was determined as the photon energy at the interception point.

Hole Drift Mobility Measurements

The samples for the hole mobility measurements were prepared by spin-coating the solutions of the synthesized compounds on the polyester films with conductive Al layer. The layer thickness was in the range of 5-10 μm. The hole drift mobility was measured by xerographic time of flight technique (XTOF). Electric field was created by positive corona charging. The charge carriers wore generated at the layer surface by illumination with pulses of nitrogen laser (pulse duration was 2 ns, wavelength 337 nm). The layer surface potential decrease as a result of pulse illumination was up to 1-5% of initial potential before illumination. The capacitance probe that was connected to the wide frequency band electrometer measured the speed of the surface potential decrease dU/di. The transit time $t_t$ was determined by the kink on the curve of the dU/dt transient in double logarithmic scale. The drift mobility was calculated by the formula $\mu=d^2/U_0t_t$, where d is the layer thickness, $U_0$—the surface potential at the moment of illumination.

TABLE 1

Ionization potential and charge mobility values of the Hole Transporting Materials

| No. | Formula | Ip, eV | Mobility $\mu_0$, cm$^2$V$^{-1}$s$^{-1}$ (at 0 V/cm) | Mobility cm$^2$V$^{-1}$s$^{-1}$ (at 6.4 · 10$^5$ V/cm) |
|---|---|---|---|---|
| V-886 | | 5.04 | 2 · 10$^{-5}$ | 6 · 10$^{-4}$ |
| V-885 | | 5.06 | 1 · 10$^{-4}$ | 4.6 · 10$^{-3}$ |

TABLE 1-continued

Ionization potential and charge mobility values of the Hole Transporting Materials

| No. | Formula | Ip, eV | Mobility $\mu_0$, cm$^2$V$^{-1}$s$^{-1}$ (at 0 V/cm) | Mobility cm$^2$V$^{-1}$s$^{-1}$ (at 6.4 · 10$^5$ V/cm) |
|---|---|---|---|---|
| V-911 | | 5.07 | 8 · 10$^{-6}$ | 4 · 10$^{-5}$ |
| V-931 | | 5.20 | — | — |

TABLE 1-continued

Ionization potential and charge mobility values of the Hole Transporting Materials

| No. | Formula | Ip, eV | Mobility $\mu_0$, $cm^2V^{-1}s^{-1}$ (at 0 V/cm) | Mobility $cm^2V^{-1}s^{-1}$ (at $6.4 \cdot 10^5$ V/cm) |
|---|---|---|---|---|
| V-928 | | 5.25 | — | — |
| V-908 | | 5.20 | $1.3 \cdot 10^{-5}$ | $4 \cdot 10^{-4}$ |

Functional groups attached at the ends of the molecules have noticeable influence on ionization potential, HTMs with methoxy groups have lower $I_p$ compared with methyl containing ones. Shape of the molecule and way of packing in the film has influence on the hole mobility results.

The invention claimed is:

1. A compound of formula (I), comprising:

(I)

wherein n is 2, 3, 4, 6 or 8;

Q is a mono- or polycyclic system comprising at least one pair of a conjugated double bond (—C=C—C=C—), the polycyclic system comprising fused aromatic rings or monocyclic aromatic rings bound together by covalent bond, said mono- or polycyclic system being substituted by H, halogen, cyano group, C1-C20 cyanoalkyl group, C1-C20 alkyl, C1-C20 alkoxy group, C1-C20 alkoxyalkyl, C1-C20 haloalkyl group, C1-C20 haloalkoxyalkyl, wherein said cyanoalkyl, alkyl, alkoxy, alkoxyalkyl, haloalkyl, haloalkoxyalkyl, if they comprise 3 or more carbons, may be linear, branched or cyclic, wherein halogen is selected from Cl, F, Br, or I, and wherein Q is linked to D through a methylene bridge, divalent alkyl or methanediyl bond —CH$_2$—;

D is a heteroaromatic polycyclic system being independently selected from formula (1) or (2):

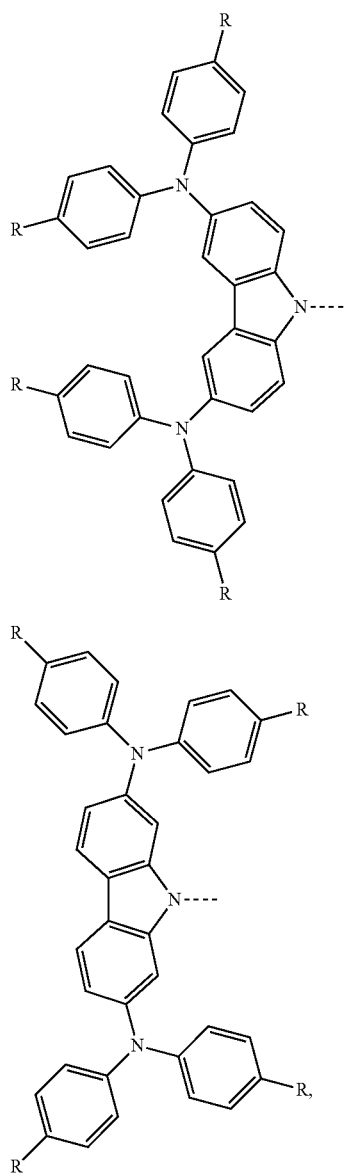

wherein
the dotted lines represent the bond by which D is connected to methylene bridge or methanediyl bond —CH$_2$—;
R is a substituent, on each occurrence, identically or differently selected from halogen, C1-C9 alkoxy group, C1-C9 alkoxyalkyl, C1-C9 alkyl group, C1-C9 haloalkoxy group, C1-C9 haloalkoxy alkyl, C1-C9 haloalkyl, C4-C20 aryl, C4-C20 heteroaryl, C4-C20 alkylaryl group, C4-C20 aryloxy group or C4-C20 heteroaryloxy group, wherein heteroatoms being selected from O, S, Se, Si and halogen being F or Cl; wherein said alkyl, alkoxy, alkoxylalkyl, haloalkyl, haloalkoxy and haloalkoxyalkyl, if they comprise 3 or more carbons, may be linear, branched or cyclic and wherein said heteroaryl, aryloxy group, heteroaryloxy group are unsubstituted or substituted by C1-C20 alkyl or C1-C20 heteroalkyl, wherein said alkyl and heteroalkyl, if they comprise 3 or more carbons, may be linear, branched or cyclic.

2. The compound of formula (I) according to claim 1 comprising a structure selected from any one of formulae (II) to (VI)

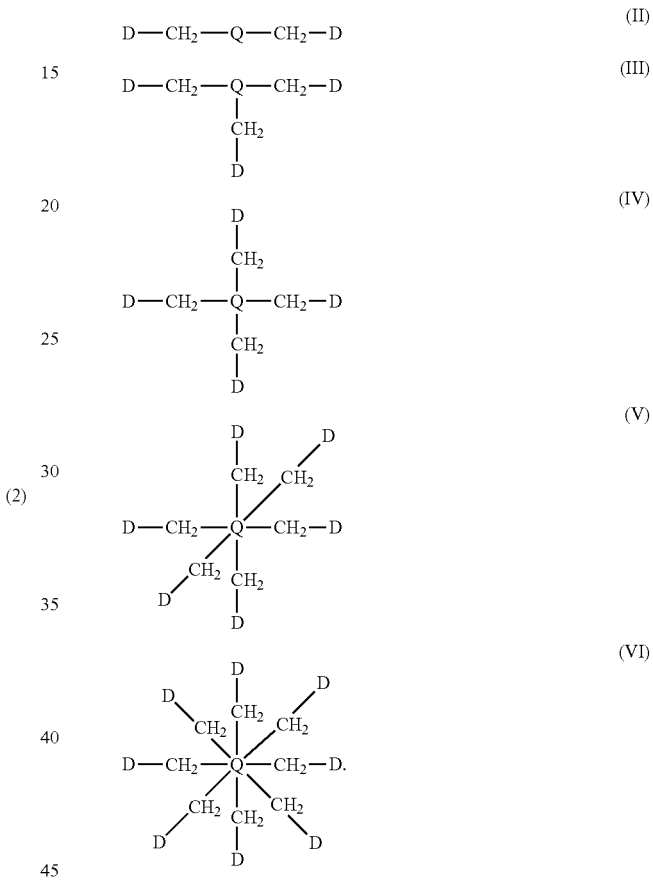

3. The compound according to claim 1, wherein Q is selected from a moiety according to any one of the formulae (3) to (20)

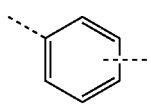

(3)

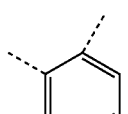

(4)

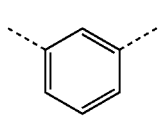

(5)

(6) 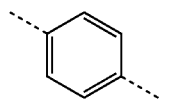

(7) 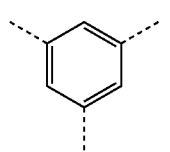

(8) 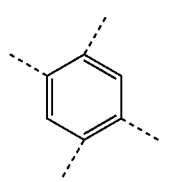

(9) 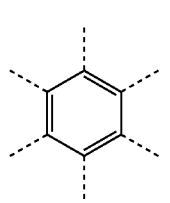

(10) 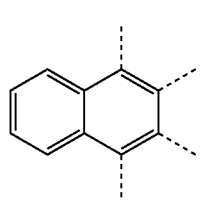

(11) 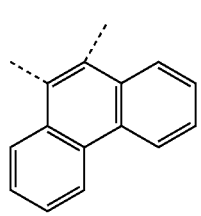

(12) 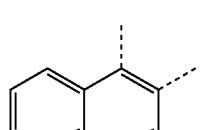

(13) 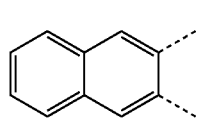

(14) 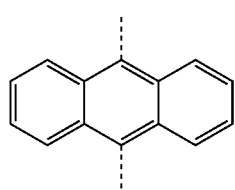

(15) 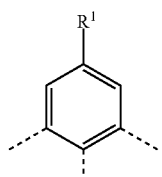

(16) 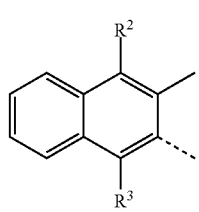

(17) 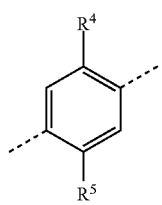

(18) 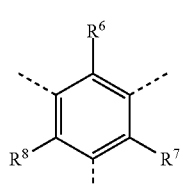

(19) 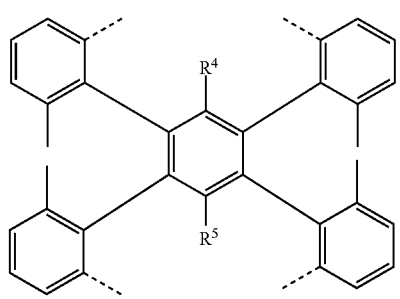

(20) 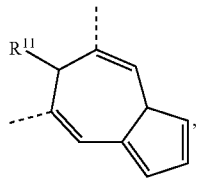

wherein
the dotted lines represent the bond by which Q is connected to methylene bridge or methanediyl bond —CH$_2$—;
$R^1$ to $R^{11}$ are substituents independently selected from H, halogen, cyano group, cyanoalkyl group, C1-C20 alkyl, C1-C20 alkoxy group, C1-C20 alkoxyalkyl, C1-C9 haloalkoxy group or C1-C9 haloalkoxyalkyl, wherein said alkyl, cyanoalkyl and alkoxyalkyl, if they comprise 3 or more carbons, may be linear, branched or cyclic and wherein halogen are selected from Cl, F, Br or I.

4. The compound according to claim 1, wherein D is a heteroaromatic polycyclic system of formula (1).

5. The compound according to claim 1, wherein D is a heteroaromatic polycyclic system of formula (2).

6. The compound according to claim 3, wherein, if n is 2, Q is selected from a moiety according to any one of formulae (3) to (6), (11) to (14), (16) and (17); if n is 3, Q is selected from a moiety according to any one of formulae (7), (15) and (18); if n is 4, Q is selected from a moiety according to any one of formulae (8) and (10); if n is 6, Q is selected from a moiety according to f formula (9); if n is 8, Q is selected from a moiety according to f formula (19).

7. The compound according to claim 1, wherein substituents R of heteroaromatic poly cyclic systems D according to any one of formulae (1) or (2) are identical.

8. The compound according to claim 1, wherein R is a substituent, on each occurrence, identically selected from halogen, C1-C9 alkyl, C1-C9 alkoxy group, C1-C9 alkoxyalkyl, C1-C9 haloalkoxy group or C1-C9 haloalkoxyalkyl group, said alkyl, alkoxy, alkoxylalkyl, haloalkyl, haloalkoxy and haloalkoxyalkyl, if they comprise 3 or more carbons, are linear, branched or cyclic.

9. A hole transporting material comprising at least one small molecule hole transporting material being selected from one of compounds of formula (I) according to claim 1.

10. An optoelectronic and/or photoelectrochemical device comprising a compound of formula (I) according to claim 1.

11. The optoelectronic and/or photoelectrochemical device according to claim 10 comprising a hole transporting material, wherein said hole transporting material comprises the compound of formula (I).

12. The optoelectronic and/or photoelectrochemical device according to claim 10 wherein the compound of formula (I) is a hole transporting material.

13. The optoelectronic and/or photoelectrochemical device according to claim 10 is selected from an organic photovoltaic device, a photovoltaic solid state device, an p-n heterojunction, an organic solar cell, a dye sensitized solar cell, a solid state solar cell, a phototransistor and OLED (organic light-emitting diode).

14. The optoelectronic and/or photoelectrochemical device according to claim 13 being a photovoltaic solid state device, which is a solid state solar cell comprising an organic-inorganic perovskite as sensitizer under the form of a layer.

15. The optoelectronic and/or photoelectrochemical device according to claim 14, wherein the organic-inorganic perovskite layer material comprises a perovskite-structure of any one of formulae (VII), (VIII), (IX), (X), (XI) and/or (XII) below:

$$AA'MX_4 \qquad (VII)$$

$$AMX_3 \qquad (VIII)$$

$$AA'N_{2/3}X_4 \qquad (IX)$$

$$AN_{2/3}X_3 \qquad (X)$$

$$BN_{2/3}X_4 \qquad (XI)$$

$$BMX_4 \qquad (XII),$$

wherein
- A and A' are organic, monovalent cations that are independently selected from primary, secondary, tertiary or quaternary organic ammonium compounds, including N-containing heterorings and ring systems, A and A' having independently from 1 to 60 carbons and 1 to 20 heteroatoms;
- B is an organic, bivalent cation selected from primary, secondary, tertiary or quaternary organic ammonium compounds having from 1 to 60 carbons and 2-20 heteroatoms and having two positively charged nitrogen atoms;
- M is a divalent metal cation selected from the group consisting of $Cu^{2+}$, $Ni^{2+}$, $Co^{2+}$, $Fe^{2+}$, $Mn^{2+}$, $Cr^{2+}$, $Pd^{2+}$, $Cd^{2+}$, $Ge^{2+}$, $Sn^{2+}$, $Pb^{2+}$, $Eu^{2+}$, or $Yb^{2+}$;
- N is selected from the group of $Bi^{3+}$ and $Sb^{3+}$; and,
- X is independently selected from $Cl^-$, $Br^-$, $I^-$, $NCS^-$, and $NCO^-$.

* * * * *

UNITED STATES PATENT AND TRADEMARK OFFICE
CERTIFICATE OF CORRECTION

PATENT NO. : 10,680,180 B2
APPLICATION NO. : 15/554373
DATED : June 9, 2020
INVENTOR(S) : Paul Gratia et al.

Page 1 of 1

It is certified that error appears in the above-identified patent and that said Letters Patent is hereby corrected as shown below:

Column 32
- Line 43: "... EP 111161954.0 ..." to be replaced with "... EP 11161954.0 ..."

Column 40
- Line 59: "... The obtained produce ..." to be replaced with "... The obtained product ..."

Column 41
- Line 14: "... After cooling to mom ..." to be replaced with "... After cooling to room ..."

Column 42
- Line 31: "... 4,440 -dimethoxydiphenylamine ..." to be replaced with "... 4,4' -dimethoxydiphenylamine ..."

Column 43
- Line 15: "... (176 MHz, DMSO-3$_6$) ..." to be replaced with "... (176 MHz, DMSO-d$_6$) ..."

Column 55
- Claim 7, Line 12: "... heteroaromatic poly cyclic systems D ..." to be replaced with "... heteroaromatic polycyclic systems D ..."

Signed and Sealed this
Twenty-eighth Day of July, 2020

Andrei Iancu
*Director of the United States Patent and Trademark Office*